US008124335B2

(12) United States Patent
Marlowe et al.

(10) Patent No.: US 8,124,335 B2
(45) Date of Patent: Feb. 28, 2012

(54) COMPOSITIONS AND ASSAYS TO DETECT INFLUENZA VIRUS A AND B NUCLEIC ACIDS

(75) Inventors: Elizabeth M. Marlowe, Encino, CA (US); Paul M. Darby, San Diego, CA (US); Damon K. Getman, Poway, CA (US); Sylvia A. Norman, Poway, CA (US); Reinhold B. Pollner, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 14 days.

(21) Appl. No.: 11/418,931

(22) Filed: May 4, 2006

(65) Prior Publication Data

US 2006/0257860 A1 Nov. 16, 2006

Related U.S. Application Data

(60) Provisional application No. 60/678,508, filed on May 6, 2005.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ...... 435/6.1; 435/91.1; 435/91.2; 536/23.1; 536/24.3

(58) Field of Classification Search ............... None
See application file for complete search history.

(56) References Cited

U.S. PATENT DOCUMENTS

| | | | |
|---|---|---|---|
| 5,187,060 A | 2/1993 | Cerutti et al. | |
| 5,541,308 A * | 7/1996 | Hogan et al. | 536/23.1 |
| 5,585,481 A | 12/1996 | Arnold, Jr. et al. | |
| 5,639,604 A * | 6/1997 | Arnold et al. | 435/6 |
| 6,015,664 A | 1/2000 | Henrickson et al. | |
| 6,623,920 B1 * | 9/2003 | Bee et al. | 435/5 |
| 6,811,971 B2 | 11/2004 | Klepp et al. | |
| 6,881,835 B2 | 4/2005 | Bai et al. | |
| 2002/0081567 A1 | 6/2002 | Henrickson et al. | |
| 2004/0029111 A1 * | 2/2004 | Linnen et al. | 435/5 |
| 2004/0142319 A1 | 7/2004 | Yu et al. | |
| 2006/0003352 A1 | 1/2006 | Lipkin et al. | |
| 2006/0014140 A1 | 1/2006 | Boivin | |
| 2006/0177849 A1 | 8/2006 | Oh et al. | |
| 2009/0111089 A1 | 4/2009 | Lindstrom et al. | |

FOREIGN PATENT DOCUMENTS

| | | |
|---|---|---|
| CA | 2 231 271 A1 | 9/1998 |
| EP | 1327691 A2 | 7/2003 |
| WO | WO97/16570 A1 | 5/1997 |
| WO | 0017391 A1 | 3/2000 |
| WO | WO00/17391 A1 | 3/2000 |
| WO | WO02/00884 A2 | 1/2002 |
| WO | WO2004/057021 A2 | 7/2004 |
| WO | 2005/005658 A1 | 1/2005 |
| WO | 2005/038039 A1 | 4/2005 |
| WO | 2005100611 A2 | 10/2005 |
| WO | 2006/116082 A1 | 11/2006 |
| WO | 2006/121773 A2 | 11/2006 |

OTHER PUBLICATIONS

Matsuzaki, et al. J Med Virol. 2004 Sep.;74(1):132-40.*
Luo, et al. Arch Virol 1999; 144:1881-1891.*
Braasch, et al. Chem Biol. Jan. 2001;8(1):1-7.*
Buck et al, Biotechniques (1999) 27(3):528-536.*
Tordo, et al. Nucleic Acids Research, 1986, vol. 14, No. 6 2671-2683.*
Latorra et al., "Design considerations and effects of LNA in PCR primers," Mol. Cell Probes, 2003,17:263.259, Academic Press Limited, USA.
Boivin et al., "Multiplex Real-Time PCR Assay for Detection of influenza and Human Respiratory Syncytial Viruses", J. Clin. Microbiol., 2004, 42(1):45-51, Am. Society for Microbiology, Washington, D.C., USA.
Collins et al., "Detection of highly pathogenic and low pathogenic avian influenza sybtype H5 (Eurasian lineage) using NASBA", J. Virol. Methods, 2002, 103:213-225, Elsevier Science B.V., Amsterdam, Netherlands.
Fouchier et al., "Detection of Influenza A Viruses from Different Species by PCR amplification of Conserved Sequences in the Matrix Gene", J. Clin. Microbiol., 2000, 38(11):4096-4101, Am. Society for Microbiology, Washington, D.C., USA.
Frisbie et al., "Surveillance of Childhood Influenza Virus Infection: What Is the Best Diagnostic Method To Use for Archival Samples?", J. Clin. Microbiol., 2004, 42(3):1181-1184, Am. Society for Microbiology, Washington, D.C., USA.
Habib-Bein et al., "Comparison of SmartCycler Real-Time Reverse Transcription-PCR Assay in a Public Health Laboratory with Direct Immunofluorescence and Cell Culture Assays in a Medical Center for Detection of Influenza A Virus", J. Clin. Microbiol., 2003, 41(8):3597-3601, Am. Society for Microbiology, Washington, D.C., USA.
Hindiyeh et al., "Evaluation of a Multiplex Real-Time Reverse Transcriptase PCR Assay for Detection and Differentiation of Influenza Viruses A and B during the 2001-2002 Influenza Season in Israel", J. Clin. Microbiol., 2005, 43(2):589-595, Am. Society for Microbiology, Washington, D.C., USA.
Kehl et al., "Evaluation of the Hexaplex Assay for Detection of Respiratory Viruses in Children", J. Clin. Microbiol., 2001, 39(5):1696-1701, Am. Society for Microbiology, Washington, D.C., USA.
Li et al., "Typing and Subtyping Influenza Virus Using DNA Microarrays and Multiplex Reverse Transcriptase PCR", J. Clin. Microbiol., 2001, 39(2):696-704, Am. Society for Microbiology, Washington, D.C., USA.

(Continued)

*Primary Examiner* — Jehanne Sitton
(74) *Attorney, Agent, or Firm* — Christine A. Gritzmacher; Heather M. Osborne; Jeffrey E. Landes

(57) ABSTRACT

Methods for detecting influenza virus A and influenza virus B nucleic acids in biological samples by using in vitro amplification and detection are disclosed. Compositions that are target-specific nucleic acid sequences and kits comprising target-specific nucleic acid oligomers for amplifying in vitro influenza virus A or influenza virus B nucleic acid and detecting amplified nucleic acid sequences are disclosed.

30 Claims, 2 Drawing Sheets

OTHER PUBLICATIONS

Lindstrom et al., "Comparative Analysis of Evolutionary Mechanisms of the Hemagglutinin and Three Internal Protein Genes of Influenza B Virus: Multiple Cocirculating Lineages and Frequent Reassortment of the NP, M, and NS Genes" J. Virol., 73(5):4413-4426, Am. Society for Microbiology, Washington, D.C., USA.

McCullers et al., "Multiple Genotypes of Influenza B Virus Circulated between 1979 and 2003", J. Virol., 2004, 78 (23):12817-12828, Am. Society for Microbiology, Washington, D.C., USA.

Moore et al., "Development and Evaluation of a Real-Time Nucleic Acid Sequence Based Amplification Assay for Rapid Detection of Influenza A", J. of Med. Virol., 2004, 74:619-628, Wiley-Liss, Inc., New York, New York, USA.

Schweiger et al., "Application of a Fluorogenic PCR Assay for Typing and Subtyping of Influenza Viruses in Respiratory Samples", J. Clin. Microbiol., 2000, 38(4):1552-1558, Am. Society for Microbiology, Washington, D.C., USA.

Stockton et al., "Multiplex PCR for Typing and Subtyping Influenza and Respiratory Syncytial Viruses", J. Clin. Microbiol., 1998, 36(10):2990-2995, Am. Society for Microbiology, Washington, D.C., USA.

Templeton et al., "Rapid and Sensitive Method Using Multiplex Real-Time PCR for Diagnosis of Infections by Influenza A and Influenza B Viruses, Respiratory Syncytial Virus, and Parainfluenza Viruses 1, 2, 3, and 4", J. Clin. Microbiol., 2004, 42(4):1564-1569, Am. Society for Microbiology, Washington, D.C., USA.

Van Elden et al., "Simultaneous Detection of Influenza Viruses A and B Using Real-Time Quantitative PCR", J. Clin. Microbiol., 2001, 39(1):196-200, Am. Society for Microbioloby, Washington, D.C., USA.

Wright et al., "Typing and Subtyping of Influenza Viruses in Clinical Samples by PCR", J. Clin. Microbiol., 1995, 33 (5):1180-1184, Am. Society for Microbiology, Washington, D.C., USA.

Singleton P. et al., "Nucleic Acid Amplification II: NASBA, TMA, SDA Ed," DNA Methods in Clinical Microbiology, 2000, Chapter 5, pp. 126-151, XP009123236, Kluwer, NL.

Lau L-T, et al., "Nucleic Acid Sequence-based amplification methods to detect avian influenza virus," BioChemical and Biophysical Research Communications, Jan. 2000, vol. 313(No. 2), pp. 336-342, Academic Press, Orlando, FL USA.

International Search Report for PCT/US2006/017210 dated Jan. 26, 2007. (5 pages).

Written Opinion of the International Searching Authority for PCT/US2006/017210 dated Jan. 26, 2007. (6 pages).

International Preliminary Report on Patentability for PCT/US2006/017210 dated Nov. 6, 2007. (7 pages).

EP Supplementary Search Report for in related EP Application EP 06 75 9067 dated Nov. 24, 2009. (13 pages).

Examiner's Report received in AU Patent Application 2006244460 dated Jul. 20, 2009. (4 pages).

* cited by examiner

SEQUENCE LISTING

<160> NUMBER OF SEQ ID NOS: 73

<210> SEQ ID NO 1
<211> LENGTH: 126
<212> TYPE: DNA
<213> ORGANISM: Influenza A virus

<400> SEQUENCE: 1
catggaatgg ctaaagacaa gaccaatcct gtcacctctg actaagggga ttttaggatt      60
tgtgttcacg ctcaccgtgc ccagtgagcg aggactgcag cgtagacgct ttgtccaaaa     120
tgccct                                                                126

<210> SEQ ID NO 2
<211> LENGTH: 21
<212> TYPE: RNA
<213> ORGANISM: Artificial
<220> FEATURE:
<223> OTHER INFORMATION: Synthetic Influenza A virus target

<400> SEQUENCE: 2
ccucgcucac ugggcacggu g                                                21

<210> SEQ ID NO 3
<211> LENGTH: 26
<212> TYPE: DNA
<213> ORGANISM: Artificial
<220> FEATURE:
<223> OTHER INFORMATION: Synthetic oligonucleotide

<400> SEQUENCE: 3
gaggcccatg caactggcaa gtgcac                                           26

<210> SEQ ID NO 4
<211> LENGTH: 28
<212> TYPE: DNA
<213> ORGANISM: Artificial
<220> FEATURE:
<223> OTHER INFORMATION: Synthetic oligonucleotide

<400> SEQUENCE: 4
gaatccacaa tatcaagtgc aagatccc                                         28

<210> SEQ ID NO 5
<211> LENGTH: 59
<212> TYPE: DNA
<213> ORGANISM: Artificial
<220> FEATURE:
<223> OTHER INFORMATION: Synthetic oligonucleotide for capture probe

<400> SEQUENCE: 5
gaggcccatg caactggcaa gtgcacttta aaaaaaaaa aaaaaaaaa aaaaaaaa          59

<210> SEQ ID NO 6
<211> LENGTH: 61
<212> TYPE: DNA
<213> ORGANISM: Artificial
<220> FEATURE:
<223> OTHER INFORMATION: Synthetic oligonucleotide for capture probe

<400> SEQUENCE: 6
gaatccacaa tatcaagtgc aagatccctt taaaaaaaa aaaaaaaaa aaaaaaaaa         60 a                                                                     61

```
<210> SEQ ID NO 7
<211> LENGTH: 49
<212> TYPE: DNA
<213> ORGANISM: Artificial
<220> FEATURE:
<223> OTHER INFORMATION: Synthetic promoter primer oligomer
<220> FEATURE:
<221> NAME/KEY: promoter
<222> LOCATION: (1)..(26)

<400> SEQUENCE: 7
aatttatacg actcactata gggagaaggg cattttggac aaakcgtct                49

<210> SEQ ID NO 8
<211> LENGTH: 49
<212> TYPE: DNA
<213> ORGANISM: Artificial
<220> FEATURE:
<223> OTHER INFORMATION: Synthetic promoter primer oligomer
<220> FEATURE:
<221> NAME/KEY: promoter
<222> LOCATION: (1)..(26)

<400> SEQUENCE: 8
aatttatacg actcactata gggagaaggg cattttggac aaagcgtct                49

<210> SEQ ID NO 9
<211> LENGTH: 49
<212> TYPE: DNA
<213> ORGANISM: Artificial
<220> FEATURE:
<223> OTHER INFORMATION: Synthetic promoter primer oligomer
<220> FEATURE:
<221> NAME/KEY: promoter
<222> LOCATION: (1)..(27)

<400> SEQUENCE: 9
aatttaatac gactcactat agggagaagg gcattttgga caaakcgtc                49

<210> SEQ ID NO 10
<211> LENGTH: 49
<212> TYPE: DNA
<213> ORGANISM: Artificial
<220> FEATURE:
<223> OTHER INFORMATION: Synthetic promoter primer oligomer
<220> FEATURE:
<221> NAME/KEY: promoter
<222> LOCATION: (1)..(27)

<400> SEQUENCE: 10
aatttaatac gactcactat agggagaagg gcattttgga caaagcgtc                49

<210> SEQ ID NO 11
<211> LENGTH: 48
<212> TYPE: DNA
<213> ORGANISM: Artificial
<220> FEATURE:
<223> OTHER INFORMATION: Synthetic promoter primer oligomer
<220> FEATURE:
<221> NAME/KEY: promoter
<222> LOCATION: (1)..(27)

<400> SEQUENCE: 11
aatttaatac gactcactat agggagaagg gcattttgga caaakcgt                 48

<210> SEQ ID NO 12
<211> LENGTH: 48
<212> TYPE: DNA
<213> ORGANISM: Artificial
```

```
<220> FEATURE:
<223> OTHER INFORMATION: Synthetic promoter primer oligomer
<220> FEATURE:
<221> NAME/KEY: promoter
<222> LOCATION: (1)..(27)

<400> SEQUENCE: 12
aatttaatac gactcactat agggagaagg gcattttgga caaagcgt                    48

<210> SEQ ID NO 13
<211> LENGTH: 23
<212> TYPE: DNA
<213> ORGANISM: Artificial
<220> FEATURE:
<223> OTHER INFORMATION: Synthetic oligomer

<400> SEQUENCE: 13
agggcatttt ggacaaakcg tct                                               23

<210> SEQ ID NO 14
<211> LENGTH: 23
<212> TYPE: DNA
<213> ORGANISM: Artificial
<220> FEATURE:
<223> OTHER INFORMATION: Synthetic oligomer

<400> SEQUENCE: 14
agggcatttt ggacaaagcg tct                                               23

<210> SEQ ID NO 15
<211> LENGTH: 22
<212> TYPE: DNA
<213> ORGANISM: Artificial
<220> FEATURE:
<223> OTHER INFORMATION: Synthetic oligomer

<400> SEQUENCE: 15
agggcatttt ggacaaakcg tc                                                22

<210> SEQ ID NO 16
<211> LENGTH: 22
<212> TYPE: DNA
<213> ORGANISM: Artificial
<220> FEATURE:
<223> OTHER INFORMATION: Synthetic oligomer

<400> SEQUENCE: 16
agggcatttt ggacaaagcg tc                                                22

<210> SEQ ID NO 17
<211> LENGTH: 21
<212> TYPE: DNA
<213> ORGANISM: Artificial
<220> FEATURE:
<223> OTHER INFORMATION: Synthetic oligomer

<400> SEQUENCE: 17
agggcatttt ggacaaakcg t                                                 21

<210> SEQ ID NO 18
<211> LENGTH: 21
<212> TYPE: DNA
<213> ORGANISM: Artificial
<220> FEATURE:
<223> OTHER INFORMATION: Synthetic oligomer

<400> SEQUENCE: 18
```

```
agggcatttt ggacaaagcg t                                              21

<210> SEQ ID NO 19
<211> LENGTH: 26
<212> TYPE: DNA
<213> ORGANISM: Bacteriophage T7
<220> FEATURE:
<221> NAME/KEY: promoter
<222> LOCATION: (1)..(26)

<400> SEQUENCE: 19
aatttatacg actcactata gggaga                                         26

<210> SEQ ID NO 20
<211> LENGTH: 27
<212> TYPE: DNA
<213> ORGANISM: Bacteriophage T7
<220> FEATURE:
<221> NAME/KEY: promoter
<222> LOCATION: (1)..(27)

<400> SEQUENCE: 20
aatttaatac gactcactat agggaga                                        27

<210> SEQ ID NO 21
<211> LENGTH: 20
<212> TYPE: DNA
<213> ORGANISM: Artificial
<220> FEATURE:
<223> OTHER INFORMATION: Synthetic oligomer

<400> SEQUENCE: 21
catggartgg ctaaagacaa                                                20

<210> SEQ ID NO 22
<211> LENGTH: 22
<212> TYPE: DNA
<213> ORGANISM: Artificial
<220> FEATURE:
<223> OTHER INFORMATION: Synthetic oligomer

<400> SEQUENCE: 22
catggartgg ctaaagacaa ga                                             22

<210> SEQ ID NO 23
<211> LENGTH: 19
<212> TYPE: DNA
<213> ORGANISM: Artificial
<220> FEATURE:
<223> OTHER INFORMATION: Synthetic oligomer

<400> SEQUENCE: 23
gtrttcacgc tcaccgtgc                                                 19

<210> SEQ ID NO 24
<211> LENGTH: 24
<212> TYPE: DNA
<213> ORGANISM: Artificial
<220> FEATURE:
<223> OTHER INFORMATION: Synthetic oligomer

<400> SEQUENCE: 24
catggartgg ctaaagacaa gacc                                           24

<210> SEQ ID NO 25
<211> LENGTH: 17
<212> TYPE: RNA
```

```
<213> ORGANISM: Artificial
<220> FEATURE:
<223> OTHER INFORMATION: Synthetic oligomer

<400> SEQUENCE: 25
caccgugccc agugagc                                                          17

<210> SEQ ID NO 26
<211> LENGTH: 16
<212> TYPE: RNA
<213> ORGANISM: Artificial
<220> FEATURE:
<223> OTHER INFORMATION: Synthetic oligomer

<400> SEQUENCE: 26
gcccagugag cgagga                                                           16

<210> SEQ ID NO 27
<211> LENGTH: 17
<212> TYPE: RNA
<213> ORGANISM: Artificial
<220> FEATURE:
<223> OTHER INFORMATION: Synthetic oligomer

<400> SEQUENCE: 27
cgaggacugc agcguag                                                          17

<210> SEQ ID NO 28
<211> LENGTH: 27
<212> TYPE: RNA
<213> ORGANISM: Artificial
<220> FEATURE:
<223> OTHER INFORMATION: Synthetic oligomer

<400> SEQUENCE: 28
ggcucgugcc cagugagcga gggagcc                                               27

<210> SEQ ID NO 29
<211> LENGTH: 27
<212> TYPE: RNA
<213> ORGANISM: Artificial
<220> FEATURE:
<223> OTHER INFORMATION: Synthetic oligomer

<400> SEQUENCE: 29
gugcccagug agcgaggacu gcggcac                                               27

<210> SEQ ID NO 30
<211> LENGTH: 28
<212> TYPE: RNA
<213> ORGANISM: Artificial
<220> FEATURE:
<223> OTHER INFORMATION: Synthetic oligomer

<400> SEQUENCE: 30
ggcuccagug agcgaggacu gcagagcc                                              28

<210> SEQ ID NO 31
<211> LENGTH: 27
<212> TYPE: RNA
<213> ORGANISM: Artificial
<220> FEATURE:
<223> OTHER INFORMATION: Synthetic oligomer

<400> SEQUENCE: 31
ggcucugagc gaggacugca gcgagcc                                               27
```

<210> SEQ ID NO 32
<211> LENGTH: 103
<212> TYPE: DNA
<213> ORGANISM: Influenza B virus

<400> SEQUENCE: 32
tcctcaactc actcttcgag cgttttaatg aaggacattc aaagccaatt cgagcagctg      60
aaactgcggt gggagtctta tcccaatttg gtcaagagca ccg                       103

<210> SEQ ID NO 33
<211> LENGTH: 34
<212> TYPE: RNA
<213> ORGANISM: Artificial
<220> FEATURE:
<223> OTHER INFORMATION: Synthetic oligomer

<400> SEQUENCE: 33
uucgguuaag cucgucgacu uugacgccac ccuc                                 34

<210> SEQ ID NO 34
<211> LENGTH: 55
<212> TYPE: DNA
<213> ORGANISM: Artificial
<220> FEATURE:
<223> OTHER INFORMATION: Synthetic capture probe oligomer

<400> SEQUENCE: 34
gucuugacca ggguagucaa ggtttaaaaa aaaaaaaaa aaaaaaaaaa aaaaa           55

<210> SEQ ID NO 35
<211> LENGTH: 53
<212> TYPE: DNA
<213> ORGANISM: Artificial
<220> FEATURE:
<223> OTHER INFORMATION: Synthetic capture probe oligomer

<400> SEQUENCE: 35
ggcucaaacc cuucaauucc tttaaaaaaa aaaaaaaaa aaaaaaaaaa aaa             53

<210> SEQ ID NO 36
<211> LENGTH: 22
<212> TYPE: RNA
<213> ORGANISM: Artificial
<220> FEATURE:
<223> OTHER INFORMATION: Synthetic oligomer

<400> SEQUENCE: 36
gucuugacca ggguagucaa gg                                              22

<210> SEQ ID NO 37
<211> LENGTH: 20
<212> TYPE: RNA
<213> ORGANISM: Artificial
<220> FEATURE:
<223> OTHER INFORMATION: Synthetic oligomer

<400> SEQUENCE: 37
ggcucaaacc cuucaauucc                                                 20

<210> SEQ ID NO 38
<211> LENGTH: 48
<212> TYPE: DNA
<213> ORGANISM: Artificial
<220> FEATURE:
<223> OTHER INFORMATION: Synthetic promoter primer oligomer
<220> FEATURE:

```
<221> NAME/KEY: promoter
<222> LOCATION: (1)..(27)

<400> SEQUENCE: 38
aatttaatac gactcactat agggagacgg tgctcttgac caaattgg          48

<210> SEQ ID NO 39
<211> LENGTH: 46
<212> TYPE: DNA
<213> ORGANISM: Artificial
<220> FEATURE:
<223> OTHER INFORMATION: Synthetic promoter primer oligomer
<220> FEATURE:
<221> NAME/KEY: promoter
<222> LOCATION: (1)..(27)

<400> SEQUENCE: 39
aatttaatac gactcactat agggagacgg tgctcttgac caaatt            46

<210> SEQ ID NO 40
<211> LENGTH: 47
<212> TYPE: DNA
<213> ORGANISM: Artificial
<220> FEATURE:
<223> OTHER INFORMATION: Synthetic promoter primer oligomer
<220> FEATURE:
<221> NAME/KEY: promoter
<222> LOCATION: (1)..(27)

<400> SEQUENCE: 40
aatttaatac gactcactat agggagacgg tgctcttgac caaattg           47

<210> SEQ ID NO 41
<211> LENGTH: 21
<212> TYPE: DNA
<213> ORGANISM: Artificial
<220> FEATURE:
<223> OTHER INFORMATION: Synthetic oligomer

<400> SEQUENCE: 41
cggtgctctt gaccaaattg g                                       21

<210> SEQ ID NO 42
<211> LENGTH: 19
<212> TYPE: DNA
<213> ORGANISM: Synthetic

<400> SEQUENCE: 42
cggtgctctt gaccaaatt                                          19

<210> SEQ ID NO 43
<211> LENGTH: 20
<212> TYPE: DNA
<213> ORGANISM: Artificial
<220> FEATURE:
<223> OTHER INFORMATION: Synthetic oligomer

<400> SEQUENCE: 43
cggtgctctt gaccaaattg                                         20

<210> SEQ ID NO 44
<211> LENGTH: 19
<212> TYPE: DNA
<213> ORGANISM: Artificial
<220> FEATURE:
<223> OTHER INFORMATION: Synthetic oligomer

<400> SEQUENCE: 44
```
tcctcaactc actcttcga                                              19

<210> SEQ ID NO 45
<211> LENGTH: 22
<212> TYPE: DNA
<213> ORGANISM: Artificial
<220> FEATURE:
<223> OTHER INFORMATION: Synthetic oligomer

<400> SEQUENCE: 45
tcctcaactc actcttcgag cg                                          22

<210> SEQ ID NO 46
<211> LENGTH: 21
<212> TYPE: DNA
<213> ORGANISM: Artificial
<220> FEATURE:
<223> OTHER INFORMATION: Synthetic oligomer

<400> SEQUENCE: 46
tcctcaactc actcttcgag c                                           21

<210> SEQ ID NO 47
<211> LENGTH: 17
<212> TYPE: DNA
<213> ORGANISM: Artificial
<220> FEATURE:
<223> OTHER INFORMATION: Synthetic oligomer

<400> SEQUENCE: 47
gaaggacatt caaagcc                                                17

<210> SEQ ID NO 48
<211> LENGTH: 17
<212> TYPE: RNA
<213> ORGANISM: Artificial
<220> FEATURE:
<223> OTHER INFORMATION: Synthetic oligomer

<400> SEQUENCE: 48
gccaauucga gcagcug                                                17

<210> SEQ ID NO 49
<211> LENGTH: 17
<212> TYPE: RNA
<213> ORGANISM: Artificial
<220> FEATURE:
<223> OTHER INFORMATION: Synthetic oligomer

<400> SEQUENCE: 49
gagcagcuga aacugcg                                                17

<210> SEQ ID NO 50
<211> LENGTH: 19
<212> TYPE: RNA
<213> ORGANISM: Artificial
<220> FEATURE:
<223> OTHER INFORMATION: Synthetic oligomer

<400> SEQUENCE: 50
gcagcugaaa cugcggugg                                              19

<210> SEQ ID NO 51
<211> LENGTH: 25
<212> TYPE: RNA
<213> ORGANISM: Artificial

<220> FEATURE:
<223> OTHER INFORMATION: Synthetic oligomer

<400> SEQUENCE: 51
cgcacgcagc ugaaacugcg gugcg                                  25

<210> SEQ ID NO 52
<211> LENGTH: 23
<212> TYPE: RNA
<213> ORGANISM: Artificial
<220> FEATURE:
<223> OTHER INFORMATION: Synthetic oligomer

<400> SEQUENCE: 52
ccagcgccaa uucgagcagc ugg                                    23

<210> SEQ ID NO 53
<211> LENGTH: 26
<212> TYPE: RNA
<213> ORGANISM: Artificial
<220> FEATURE:
<223> OTHER INFORMATION: Synthetic oligomer

<400> SEQUENCE: 53
cgguggcuga aacugcggug gcaccg                                 26

<210> SEQ ID NO 54
<211> LENGTH: 28
<212> TYPE: RNA
<213> ORGANISM: Artificial
<220> FEATURE:
<223> OTHER INFORMATION: Synthetic oligomer

<400> SEQUENCE: 54
ggcucuucga gcagcugaaa cuggagcc                               28

<210> SEQ ID NO 55
<211> LENGTH: 27
<212> TYPE: RNA
<213> ORGANISM: Artificial
<220> FEATURE:
<223> OTHER INFORMATION: Synthetic oligomer

<400> SEQUENCE: 55
ggcucucgag cagcugaaac uggagcc                                27

<210> SEQ ID NO 56
<211> LENGTH: 30
<212> TYPE: RNA
<213> ORGANISM: Artificial
<220> FEATURE:
<223> OTHER INFORMATION: Synthetic oligomer

<400> SEQUENCE: 56
ggcucauucg agcagcugaa acugugagcc                             30

<210> SEQ ID NO 57
<211> LENGTH: 30
<212> TYPE: RNA
<213> ORGANISM: Artificial
<220> FEATURE:
<223> OTHER INFORMATION: Synthetic oligomer

<400> SEQUENCE: 57
ggcucguucg agcagcugaa acugcgagcc                             30

```
<210> SEQ ID NO 58
<211> LENGTH: 24
<212> TYPE: RNA
<213> ORGANISM: Artificial
<220> FEATURE:
<223> OTHER INFORMATION: Synthetic oligomer

<400> SEQUENCE: 58
cgcagucgag cagcugaaac ugcg                                        24

<210> SEQ ID NO 59
<211> LENGTH: 57
<212> TYPE: DNA
<213> ORGANISM: Artificial
<220> FEATURE:
<223> OTHER INFORMATION: Synthetic capture probe oligomer

<400> SEQUENCE: 59
cguucacuau uggucucugc auucuuuaaa aaaaaaaaa aaaaaaaaa aaaaaaa      57

<210> SEQ ID NO 60
<211> LENGTH: 24
<212> TYPE: RNA
<213> ORGANISM: Artificial
<220> FEATURE:
<223> OTHER INFORMATION: Synthetic oligomer

<400> SEQUENCE: 60
cguucacuau uggucucugc auuc                                        24

<210> SEQ ID NO 61
<211> LENGTH: 47
<212> TYPE: DNA
<213> ORGANISM: Artificial
<220> FEATURE:
<223> OTHER INFORMATION: Synthetic promoter primer oligomer
<220> FEATURE:
<221> NAME/KEY: promoter
<222> LOCATION: (1)..(27)

<400> SEQUENCE: 61
aatttaatac gactcactat agggagacat gtcccaattc gcaccag                47

<210> SEQ ID NO 62
<211> LENGTH: 21
<212> TYPE: DNA
<213> ORGANISM: Artificial
<220> FEATURE:
<223> OTHER INFORMATION: Synthetic oligomer

<400> SEQUENCE: 62
ctatatactc aaggaagtga c                                           21

<210> SEQ ID NO 63
<211> LENGTH: 26
<212> TYPE: RNA
<213> ORGANISM: Artificial
<220> FEATURE:
<223> OTHER INFORMATION: Synthetic oligomer

<400> SEQUENCE: 63
ccgagcaagu guacuagccg acucgg                                      26

<210> SEQ ID NO 64
<211> LENGTH: 47
<212> TYPE: DNA
<213> ORGANISM: Artificial
<220> FEATURE:
```

```
<223> OTHER INFORMATION: Synthetic promoter primer oligomer
<220> FEATURE:
<221> NAME/KEY: promoter
<222> LOCATION: (1)..(27)

<400> SEQUENCE: 64
aatttaatac gactcactat agggagaatt gaccatgtcc caattcg        47

<210> SEQ ID NO 65
<211> LENGTH: 251
<212> TYPE: DNA
<213> ORGANISM: Artificial
<220> FEATURE:
<223> OTHER INFORMATION: Synthetic oligomer

<400> SEQUENCE: 65
tcattcatca taactatata ctcaaggaag tgacaataga ttatatagga cgacaagtaa      60
aaattaaaac atcgcaagtg tactagccga tggtcgtgcc tggtgcgaat tgggacatgg    120
tcaattagag acaaagaaga gcggaatcac aagtcaatca tcgcgcaaga tagaggaaat    180
aaaataggaa caagtaagaa caatagaaat catagaatgc agagaccaat agtgaacgta    240
aagaccaagt t                                                         251

<210> SEQ ID NO 66
<211> LENGTH: 47
<212> TYPE: DNA
<213> ORGANISM: Artificial
<220> FEATURE:
<223> OTHER INFORMATION: Synthetic promoter primer oligomer
<220> FEATURE:
<221> NAME/KEY: promoter
<222> LOCATION: (1)..(27)

<400> SEQUENCE: 66
aatttaatac gactcactat agggagagac ttgtgattcc gctcttc        47

<210> SEQ ID NO 67
<211> LENGTH: 51
<212> TYPE: DNA
<213> ORGANISM: Artificial
<220> FEATURE:
<223> OTHER INFORMATION: Synthetic promoter primer oligomer
<220> FEATURE:
<221> NAME/KEY: promoter
<222> LOCATION: (1)..(27)

<400> SEQUENCE: 67
aatttaatac gactcactat agggagagat gattgacttg tgattccgct c    51

<210> SEQ ID NO 68
<211> LENGTH: 24
<212> TYPE: DNA
<213> ORGANISM: Artificial
<220> FEATURE:
<223> OTHER INFORMATION: Synthetic oligomer

<400> SEQUENCE: 68
catggartgg ctaaagacaa gacc        24

<210> SEQ ID NO 69
<211> LENGTH: 24
<212> TYPE: DNA
<213> ORGANISM: Artificial
<220> FEATURE:
<223> OTHER INFORMATION: Synthetic oligomer

<400> SEQUENCE: 69
```

```
agggcatttt ggacaaakcg tcta                                          24

<210> SEQ ID NO 70
<211> LENGTH: 24
<212> TYPE: DNA
<213> ORGANISM: Artificial
<220> FEATURE:
<223> OTHER INFORMATION: Synthetic oligomer

<400> SEQUENCE: 70
tgcagtcctc gctcactggg cacg                                          24

<210> SEQ ID NO 71
<211> LENGTH: 22
<212> TYPE: DNA
<213> ORGANISM: Artificial
<220> FEATURE:
<223> OTHER INFORMATION: Synthetic oligomer

<400> SEQUENCE: 71
tcctcaactc actcttcgag cg                                            22

<210> SEQ ID NO 72
<211> LENGTH: 21
<212> TYPE: DNA
<213> ORGANISM: Artificial
<220> FEATURE:
<223> OTHER INFORMATION: Synthetic oligomer

<400> SEQUENCE: 72
cggtgctctt gaccaaattg g                                             21

<210> SEQ ID NO 73
<211> LENGTH: 27
<212> TYPE: DNA
<213> ORGANISM: Artificial
<220> FEATURE:
<223> OTHER INFORMATION: Synthetic oligomer

<400> SEQUENCE: 73
ccaattcgag cagctgaaac tgcggtg                                       27
```

COMPOSITIONS AND ASSAYS TO DETECT INFLUENZA VIRUS A AND B NUCLEIC ACIDS

RELATED APPLICATION

This application claims the benefit under 35 U.S.C. 119(e) of provisional application No. 60/678,508, filed May 6, 2005, which is incorporated by reference herein.

FIELD OF THE INVENTION

The field is detection of infectious agents, more specifically by using compositions and methods to detect influenza virus A and influenza virus B sequences by using in vitro nucleic acid amplification and probe detection.

BACKGROUND OF THE INVENTION

Influenza viruses (types A, B, and C) are members of the orthomyxoviridae family that cause influenza. Type A influenza viruses infect birds and mammals, including humans, whereas types B and C infect humans only. Influenza viruses are roughly spherical enveloped viruses of about 8-200 nm diameter that contain segmented negative sense genomic RNA. The envelope contains rigid structures that include hemagglutinin (HA) and neuraminidase (NA). Combinations of HA and NA subtypes, which result from genetic resortment, are used to characterize viral isolates. Generally, influenza viral isolates are identified by nomenclature that includes type, location, isolate number, isolation year, and HA and NA subtypes (e.g., "A/Sydney/7/97(H3N2)" refers to type A, from Sydney, isolate 7, in 1997, with HA 3 and NA 2 subtypes). Minor genetic changes that produce antigenic drift may cause influenza epidemics, whereas genetic changes that result in a new HA or NA subtype produce antigenic shift that may cause a pandemic. Analysis of human influenza virus A infections has shown that a few HA and NA combinations were clinically significant in causing pandemics during the 1900s, i.e., H1N1 in 1918, H2N2 in 1957, and H3N2 in 1968.

Influenza viruses that infect birds (e.g., chickens, ducks, pigeons) use combinations of H5, H7 or H9 with any of N1 to N9. Since 1997, avian influenza viruses that have infected humans have included H5N1, H9N2, H7N2, and H7N7 viruses. Even limited human infections caused by an avian influenza virus raise concern for a potential pandemic, resulting in quarantines, and intentional destruction of large numbers of fowl, with accompanying hardship. An avian influenza virus, or variant derived therefrom, that efficiently transfers by human-to-human contact could cause a pandemic (Li et al., 2003, J. Virol. 77(12): 6988-6994).

Human influenza viruses produce highly contagious, acute respiratory disease that results in significant morbidity and economic costs, with significant mortality among very young, elderly, and immuno-compromised subpopulations. Avian influenza infections in humans generally have a high mortality rate. A typical influenza virus infection in humans has a short incubation period (1 to 2 days) and symptoms that last about a week (e.g., abrupt onset of fever, sore throat, cough, headache, myalgia, malaise and anorexia), which may lead to pneumonia. Optimal protection against infection requires annual inoculation with a vaccine that includes a compbination of types A and B of the most likely subtypes for that year, based on global epidemiological surveillance. To be effective in treatment, pharmaceuticals that block viral entry into cells or decrease viral release from infected cells must be administered within 48 hrs of symptoms onset.

A variety of methods have been used to detect influenza viruses clinically. Viral culture in vitro (in monkey kidney cells) followed by visual analysis and/or hemadsorption using microbiological methods can detect influenza viruses A and B in specimens (e.g., nasopharyngeal or throat swab, nasal or bronchial wash, nasal aspirate, or sputum). Other detection tests include immunofluorescence assays (IFA), enzyme immunoassays (EIA), and enzyme-linked immunosorbent assays (ELISA) that use antibodies specific to influenza virus antigens. Examples include a sandwich microsphere-based IFA that uses influenza A- or B-specific monoclonal antibodies and flow cytometry (Yan et al., 2004, J. Immunol. Methods 284(1-2): 27-38), monoclonal antibody-based EIA tests (DIRECTIGEN® FLU A and DIRECTIGEN® FLU A+B, Becton, Dickinson and Co., Franklin Lakes, N.J., and QUICKVUE® Influenza Test, Quidel, San Diego, Calif.), and an immunoassay that produces a color change due to increased thickness of molecular thin films when an immobilized antibody binds an influenza A or B nucleoprotein (FLU OIA®, Biostar Inc., Boulder, Colo.). Another chromagenic assay detects viral NA activity by substrate cleavage (ZSTAT FLU®, ZymeTx, Inc., Oklahoma City, Okla.). Assays are known that rely on reverse-transcriptase polymerase chain reactions (RT-PCR) to amplify influenza viral sequences to detect influenza A and B viruses (e.g., Templeton et al., 2004, J. Clin. Microbiol. 42(4):1564-69; Frisbie et al., 2004, J. Clin. Microbiol. 42(3):1181-84; Boivin et al., 2004, J. Clin. Microbiol., 42(1):45-51; Habib-Bein et al., 2003, J. Clin. Microbiol. 41(8):3597-3601; Li et al., 2001, J. Clin. Microbiol. 39(2):696-704; van Elden et al., 2001, J. Clin. Microbiol. 39(1): 196-200; Fouchier et al., 2000, J. Clin. Microbiol. 38(11):4096-101; Ellis et al., 1997, J. Clin. Microbiol. 35(8): 2076-2082; PCT Nos. WO 2004 057021, WO 02 00884, WO 00 17391, and WO 97/16570, EP Publ. No. 1 327 691 A2, U.S. Pat. No. 6,015,664, and PROFLU-1™ and HEXAPLEX™ tests, Prodesse, Milwaukee, Wis.). Serology detects seroconversion associated with influenza virus A or B infections by detecting antibodies present in acute and convalescent sera from patients with influenza symptoms. Detection methods have associated advantages and disadvantages related to sensitivity, specificity, assay and handling time, required equipment, and exposure of technical personnel to infectious agents with related safety requirements for laboratories and personnel. Generally, culture and serological tests require longer completion times (5 days to 2 weeks) with potentially greater exposure of technical personnel to infectious agents. Immunoassays are generally faster (30 min to 4 hrs) but often require substantial sample handling and rely on subjective determination of results by technical personnel. PCR-based amplification assays may take up to 2 days to complete and require specialized thermocycling equipment. Hence a need remains for a test that provides sensitive, specific detection of influenza virus type A and type B in a relatively short time, with a minimum of exposure of technical personnel to infectious agents, so that diagnosis is completed in sufficient time to permit effective therapeutic treatment of an infected person.

SUMMARY OF THE INVENTION

An embodiment disclosed herein is a composition that includes at least two nucleic acid oligomers specific for influenza virus A made up of sequences consisting of SEQ ID NO:3 to SEQ ID NO:18 and SEQ ID NO:21 to SEQ ID NO:31, or their completely complementary sequences, or DNA equivalents thereof. Preferred embodiments include nucleic acid oligomers in which at least one oligomer is selected from the sequences consisting of SEQ ID NO:7 to SEQ ID NO:18 and at least one oligomer is selected from the sequences consisting of SEQ ID NO:21 to SEQ ID NO:24. Another preferred embodiment also includes at least one oligomer selected from sequences consisting of SEQ ID NO:25 to SEQ ID NO:31. In preferred embodiments, at least one of the oligomers includes at least one 2'-methoxy RNA group, whereas in other preferred embodiments at least one of the oligomers includes at least one locked nucleic acid (LNA) residue at the 5' end of the oligomer. In a preferred embodiment that includes an oligomer selected from sequences consisting of SEQ ID NO:25 to SEQ ID NO:31, the oligomer also includes a detectable label joined directly or indirectly to the oligomer sequence. A preferred label is one that is detectable in a homogeneous assay system. Preferred embodiments of these compositions are kits that include at least two of the specified nucleic acid oligomers specific for influenza virus A.

Another embodiment disclosed herein is a composition that includes at least two nucleic acid oligomers specific for influenza virus B made up of sequences consisting of SEQ ID NO:34 to SEQ ID NO:58, or their completely complementary sequences, or DNA equivalents thereof. A preferred embodiment includes at least one oligomer selected from the sequences consisting of SEQ ID NO:38 to SEQ ID NO:43 and at least one oligomer selected from the sequences consisting of SEQ ID NO:44 to SEQ ID NO:47. Another preferred embodiment also includes at least one oligomer selected from sequences consisting of SEQ ID NO:48 to SEQ ID NO:58. In some preferred embodiments, at least one of the oligomers includes at least one 2'-methoxy RNA group, whereas in other preferred embodiments, at least one of the oligomers includes at least one locked nucleic acid (LNA) residue at the 5' end of the oligomer. In a preferred embodiment, the oligomer selected from sequences consisting of SEQ ID NO:48 to SEQ ID NO:58 includes a detectable label joined directly or indirectly to the oligomer sequence. Preferred embodiments include a label that is detectable in a homogeneous assay system. Preferred embodiments of the compositions are kits that include at least two of the specified nucleic acid oligomers specific for influenza virus B.

Another embodiment is a method of detecting nucleic acid of influenza virus A or influenza virus B in a sample, that includes the steps of amplifying a target sequence in an influenza virus A nucleic acid or influenza virus B nucleic acid contained in a sample by using a nucleic acid polymerase in vitro to produce an amplified product under substantially isothermal conditions, wherein the target sequence of influenza virus A is contained in SEQ ID NO:1, or its complete complementary sequence, or RNA equivalents thereof, and wherein the target sequence of influenza virus B is contained in SEQ ID NO:32, or its complete complementary sequence, or RNA equivalents thereof, and detecting the amplified product. In a preferred embodiment, the step of amplifying the target sequence of influenza virus A uses at least one oligomer selected from sequences consisting of SEQ ID NO:7 to SEQ ID NO:18 and one oligomer selected from sequences consisting of SEQ ID NO:21 to SEQ ID NO:24. In another embodiment, the step of amplifying the target sequence of influenza virus B uses at least one oligomer selected from sequences consisting of SEQ ID NO:38 to SEQ ID NO:43 and one oligomer selected from sequences consisting of SEQ ID NO:44 to SEQ ID NO:47. In another preferred embodiment, the detecting step uses at least one probe selected from the sequences consisting of SEQ ID NO:25 to SEQ ID NO:31 to detect the amplified product of the target sequence of influenza virus A, or at least one probe selected from the sequences consisting of SEQ ID NO:48 to SEQ ID NO:58 to detect the amplified product of the target sequence of influenza virus B. A preferred embodiment of the method also includes the steps of providing an internal control oligomer, amplifying a target sequence contained in the internal control oligomer, and detecting the amplified product made from the internal control oligomer, thereby indicating that the amplifying and detecting steps of the method were properly performed. In another preferred embodiment, the method also includes isolating an influenza virus nucleic acid from the sample containing the influenza virus A nucleic acid or influenza virus B nucleic acid before the amplifying step.

DETAILED DESCRIPTION OF THE INVENTION

Figure 1:
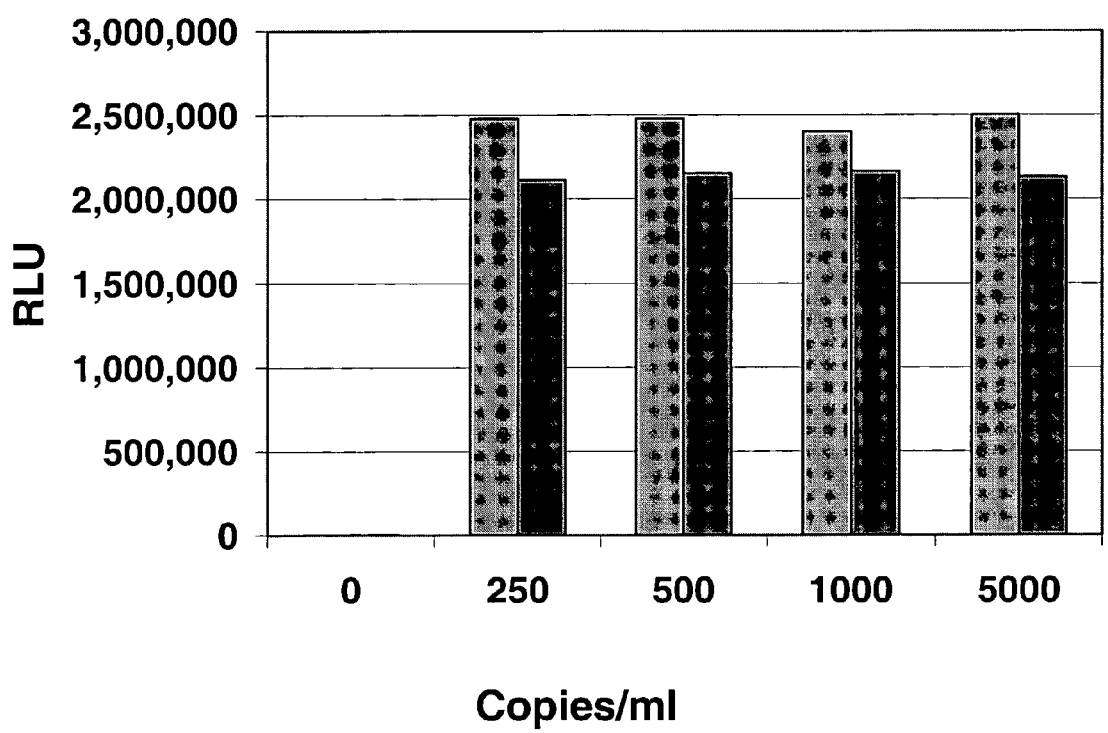
FIG. 1 is a bar graph showing signal detected (relative light units, RLU) for different amounts of influenza virus A target (250 to 5000 copies per ml) in TMA-based assays performed manually (light bars) or by using an automated system (dark bars).

Nucleic acid oligomer sequences are disclosed that may serve as primers for amplification of influenza virus type A and influenza virus type B nucleic acids present in samples by using methods of in vitro nucleic acid amplification, preferably by using a transcription-mediated amplification reaction such as TMA or NASBA, and probes for detection of the amplified nucleic acid sequences. Detection probes hybridize specifically to a portion of the amplified viral sequence, either after completion of or during the amplification process. Some embodiments detect the amplified products by using a homogeneous detection method that detects, in a mixture, a labeled probe bound specifically to an amplified sequence (e.g., see Arnold et al., 1989, *Clin. Chem.* 35:1588-1594; U.S. Pat. No. 5,658,737, Nelson et al., and U.S. Pat. Nos. 5,118,801 and 5,312,728, Lizardi et al.). Embodiments of the methods also use oligonucleotide sequences that serve as capture probes for processing a sample to capture the target influenza virus nucleic acid and separate it from other sample components (U.S. Pat. Nos. 6,110,678, 6,280,952 and 6,534,273, Weisburg et al.).

Methods disclosed herein detect influenza virus A and B nucleic acids present in samples derived from humans, preferably in nasopharyngeal or throat swabs, nasal or bronchial washes, nasal aspirates, or sputum. Compositions disclosed herein include capture oligomers to separate influenza virus A or influenza virus B target nucleic acids from other components in a sample, amplification oligomers to specifically amplify selected nucleic acid sequences present in influenza virus genomic sequences, and nucleic acid probes for detecting the amplified sequences. Preferred embodiments include specific combinations of oligomers to amplify and detect influenza virus type A and type B sequences in assays that provide a detectable signal or response within about 45 min from beginning of a transcription-associated amplification reaction.

The disclosed nucleic acid sequences and methods are useful for amplifying and detecting influenza virus type A and type B nucleic acids from viral particles present in a sample in a relatively short time so that diagnosis can be made during early stages of infection (e.g., within 48 hr of symptoms) so that effective treatment can be initiated. The methods are useful for screening for individuals who have influenza virus infections but who do not exhibit definitive symptoms, particularly for screening patients who have a higher risk of death or serious complications from influenza virus infections, e.g., young, elderly, or immunocompromised individuals. The methods are also useful for rapid screening of many samples, such as during an epidemic or pandemic, so that appropriate public health responses can be initiated. The methods are useful because they minimize the risk of exposure of laboratory personnel to infectious agents, such as an avian influenza virus related to influenza virus type A or type B that has become infectious to humans. Thus, the methods and compositions disclosed herein respond to a need for rapid, sensitive, and specific testing of clinical samples that may contain influenza virus A or virus B.

A "sample" or "specimen", including "biological" or "clinical" samples, refers to a tissue or material derived from a living or dead human or animal which may contain an influenza virus target nucleic acid, including, for example, nasopharyngeal or throat swabs, nasal or bronchial washes, nasal aspirates, sputum, other respiratory tissue or exudates, or biopsy tissue including lymph nodes. A sample may be treated to physically or mechanically disrupt tissue or cell structure to release intracellular nucleic acids into a solution which may contain enzymes, buffers, salts, detergents and the like, to prepare the sample for analysis.

"Nucleic acid" refers to a multimeric compound comprising nucleosides or nucleoside analogs which have nitrogenous heterocyclic bases or base analogs linked together to form a polynucleotide, including conventional RNA, DNA, mixed RNA-DNA, and polymers that are analogs thereof. A nucleic acid "backbone" may be made up of a variety of linkages, including one or more of sugar-phosphodiester linkages, peptide-nucleic acid bonds ("peptide nucleic acids" or PNA; PCT No. WO 95/32305), phosphorothioate linkages, methylphosphonate linkages, or combinations thereof. Sugar moieties of a nucleic acid may be ribose, deoxyribose, or similar compounds with substitutions, e.g., 2' methoxy or 2' halide substitutions. Nitrogenous bases may be conventional bases (A, G, C, T, U), analogs thereof (e.g., inosine or others; see *The Biochemistry of the Nucleic Acids* 5-36, Adams et al., ed., $11^{th}$ ed., 1992), derivatives of purines or pyrimidines (e.g., $N^4$-methyl deoxygaunosine, deaza- or aza-purines, deaza- or aza-pyrimidines, pyrimidine bases with substituent groups at the 5 or 6 position, purine bases with a substituent at the 2, 6 or 8 positions, 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines; U.S. Pat. No. 5,378,825 and PCT No. WO 93/13121). Nucleic acids may include one or more "abasic" residues where the backbone includes no nitrogenous base for position(s) of the polymer (U.S. Pat. No. 5,585,481). A nucleic acid may comprise only conventional RNA or DNA sugars, bases and linkages, or may include both conventional components and substitutions (e.g., conventional bases with 2' methoxy linkages, or polymers containing both conventional bases and one or more base analogs). Nucleic acid includes "locked nucleic acid" (LNA), an analogue containing one or more LNA nucleotide monomers with a bicyclic furanose unit locked in an RNA mimicking sugar conformation, which enhance hybridization affinity toward complementary RNA and DNA sequences (Vester and Wengel, 2004, *Biochemistry* 43(42):13233-41). Embodiments of oligomers that may affect stability of a hybridization complex include PNA oligomers, oligomers that include 2'-methoxy or 2'-fluoro substituted RNA, or oligomers that affect the overall charge, charge density, or steric associations of a hybridization complex, including oligomers that contain charged linkages (e.g., phosphorothioates) or neutral groups (e.g., methylphosphonates).

An "oligomer" or "oligonucleotide" refers to a nucleic acid of generally less than 1,000 nucleotides (nt), including those in a size range having a lower limit of about 2 to 5 nt and an upper limit of about 500 to 900 nt. Some preferred embodiments are oligomers in a size range with a lower limit of about 5 to 15 nt and an upper limit of about 50 to 600 nt, and other preferred embodiments are in a size range with a lower limit of about 10 to 20 nt and an upper limit of about 22 to 100 nt. Oligomers may be purified from naturally occurring sources, but preferably are synthesized by using any well known enzymatic or chemical method. Oligomers may be referred to by a functional name (e.g., capture probe, primer or promoter primer) but those skilled in the art will understand that such terms refer to oligomers.

A "capture probe", "capture oligonucleotide", or "capture oligomer" refers to a nucleic acid oligomer that specifically hybridizes to a target sequence in a target nucleic acid by standard base pairing and joins to a binding partner on an immobilized probe to capture the target nucleic acid to a support. A preferred embodiment of a capture oligomer includes two binding regions: a sequence-binding region (i.e., target-specific portion) and an immobilized probe-binding region, usually on the same oligomer, although the two regions may be present on two different oligomers joined together by one or more linkers.

An "immobilized probe", "immobilized oligomer" or "immobilized nucleic acid" refers to a nucleic acid binding partner that joins a capture oligomer to a support, directly or indirectly. An immobilized probe joined to a support facilitates separation of a capture probe bound target from unbound material in a sample. Any support may be used, e.g., matrices or particles free in solution, which may be made of any of a variety of materials, e.g., nylon, nitrocellulose, glass, polyacrylate, mixed polymers, polystyrene, silane polypropylene, or metal. Preferred embodiments use a support that is magnetically attractable particles, e.g., monodisperse paramagnetic beads (uniform size±5%) to which an immobilized probe is joined directly (e.g., via covalent linkage, chelation, or ionic interaction) or indirectly (e.g., via a linker), where the joining is stable during nucleic acid hybridization conditions.

"Separating" or "purifying" refers to removing one or more components of a sample from one or more other sample components, e.g., removing some nucleic acids from a generally aqueous solution that may also contain proteins, carbohydrates, lipids, or other nucleic acids. In preferred embodiments, a separating or purifying step removes the target nucleic acid from at least about 70%, more preferably at least about 90% and, even more preferably, at least about 95% of the other sample components.

An "amplification oligonucleotide" or "amplification oligomer" refers to an oligonucleotide that hybridizes to a target nucleic acid, or its complement, and participates in a nucleic acid amplification reaction, e.g., serving as a primer or and promoter-primer. Preferred amplification oligomers contain at least about 10 contiguous bases, and more preferably at least 12 contiguous bases, that are complementary to a region of the target nucleic acid sequence or its complementary strand. The contiguous bases are preferably at least about 80%, more preferably at least about 90%, and most preferably completely complementary to the target sequence to which the amplification oligomer binds. Preferred amplification oligomers are about 10 to about 60 bases long and optionally may include modified nucleotides. A "primer" refers to an oligomer that hybridizes to a template nucleic acid and has a 3' end that is extended by polymerization. A primer may be optionally modified, e.g., by including a 5' region that is non-complementary to the target sequence. A primer modified with a 5' promoter sequence is referred to as a "promoter-primer." A person of ordinary skill in the art of molecular biology or biochemistry will understand that an oligomer that can function as a primer can be modified to include a 5' promoter sequence and then function as a promoter-primer, and, similarly, any promoter-primer can serve as a primer with or without its 5' promoter sequence.

"Nucleic acid amplification" refers to any well known in vitro procedure that produces multiple copies of a target nucleic acid sequence, or its complementary sequence, or fragments thereof (i.e., an amplified sequence containing less than the complete target nucleic acid). Examples of well known nucleic acid amplification procedures include transcription associated methods, such as transcription-mediated amplification (TMA), nucleic acid sequence-based amplification (NASBA) and others (e.g., U.S. Pat. Nos. 5,399,491, 5,554,516, 5,437,990, 5,130,238, 4,868,105, and 5,124,246), replicase-mediated amplification (e.g., U.S. Pat. No. 4,786,600), the polymerase chain reaction (PCR) (e.g., U.S. Pat. Nos. 4,683,195, 4,683,202, and 4,800,159), ligase chain reaction (LCR) (e.g., EP Pat. App. 0320308) and strand-displacement amplification (SDA) (e.g., U.S. Pat. No. 5,422,252). Replicase-mediated amplification uses self-replicating RNA molecules, and a replicase such as QB-replicase. PCR amplification uses DNA polymerase, primers, and thermal cycling steps to synthesize multiple copies of the two complementary strands of DNA or cDNA. LCR amplification uses at least four separate oligonucleotides to amplify a target and its complementary strand by using multiple cycles of hybridization, ligation, and denaturation. SDA uses a primer that contains a recognition site for a restriction endonuclease that will nick one strand of a hemimodified DNA duplex that includes the target sequence, followed by amplification in a series of primer extension and strand displacement steps. Preferred embodiments use a transcription associated amplification, such as TMA or NASBA, but it will be apparent to persons of ordinary skill in the art that oligomers disclosed herein may be readily used as primers in other amplification methods. Briefly, transcription associated amplification uses a DNA polymerase, an RNA polymerase, deoxyribonucleoside triphosphates, ribonucleoside triphosphates, a promoter-containing oligonucleotide, and optionally may include other oligonucleotides, to ultimately produce multiple RNA transcripts from a nucleic acid template (described in detail in U.S. Pat. Nos. 5,399,491 and 5,554,516, Kacian et al., U.S. Pat. No. 5,437,990, Burg et al., PCT Nos. WO 88/01302 and WO 88/10315, Gingeras et al., U.S. Pat. No. 5,130,238, Malek et al., U.S. Pat. Nos. 4,868,105 and 5,124,246, Urdea et al., PCT No. WO 94/03472, McDonough et al., PCT No. WO 95/03430, and Ryder et al.). Preferred methods that use TMA as described in detail previously (U.S. Pat. Nos. 5,399,491 and 5,554,516).

"Detection probe" refers to a nucleic acid oligomer that hybridizes specifically to a target sequence, including an amplified sequence, under conditions that promote nucleic acid hybridization, for detection of the target nucleic acid. Detection may either be direct (i.e., probe hybridized directly to the target) or indirect (i.e., a probe hybridized to an intermediate structure that links the probe to the target). A probe's target sequence generally refers to the specific sequence within a larger sequence which the probe hybridizes specifically. A detection probe may include target-specific sequences and other sequences or structures that contribute to the probe's three-dimensional structure, depending on whether the target sequence is present (e.g., U.S. Pat. Nos. 5,118,801, 5,312,728, 6,835,542, and 6,849,412).

"Label" refers to a moiety or compound joined directly or indirectly to a probe that is detected or leads to a detectable signal. Direct joining may use covalent bonds or non-covalent interactions (e.g., hydrogen bonding, hydrophobic or ionic interactions, and chelate or coordination complex formation) whereas indirect joining may use a bridging moiety or linker (e.g., via an antibody or additional oligonucleotide(s), which amplify a detectable signal. Any detectable moiety may be used, e.g., radionuclide, ligand such as biotin or avidin, enzyme, enzyme substrate, reactive group, chromophore such as a dye or particle (e.g., latex or metal bead) that imparts a detectable color, luminescent compound (e.g. bioluminescent, phosphorescent or chemiluminescent compound), and fluorescent compound. Preferred embodiments include a "homogeneous detectable label" that is detectable in a homogeneous system in which bound labeled probe in a mixture exhibits a detectable change compared to unbound labeled probe, which allows the label to be detected without physically removing hybridized from unhybridized labeled probe (e.g., U.S. Pat. Nos. 5,283,174, 5,656,207 and 5,658,737). Preferred homogeneous detectable labels include chemiluminescent compounds, more preferably acridinium ester ("AE") compounds, such as standard AE or AE derivatives which are well known (U.S. Pat. Nos. 5,656,207, 5,658,737, and 5,639,604). Methods of synthesizing labels, attaching labels to nucleic acid, and detecting signals from labels are well known (e.g., Sambrook et al., *Molecular Cloning, A Laboratory Manual*, 2nd ed. (Cold Spring Harbor Laboratory Press, Cold Spring Harbor, N.Y., 1989) at Chapt. 10, and U.S. Pat. Nos. 5,658,737, 5,656,207, 5,547,842, 5,283,174, and 4,581,333, and EP Pat. App. 0 747 706). Preferred methods of linking an AE compound to a nucleic acid are known (e.g., U.S. Pat. Nos. 5,585,481 and 5,639,604, see column 10, line 6 to column 11, line 3, and Example 8). Preferred AE labeling positions are a probe's central region and near a region of A/T base pairs, at a probe's 3' or 5' terminus, or at or near a mismatch site with a known sequence that is the probe should not detect compared to the desired target sequence.

Sequences are "sufficiently complementary" if they allow stable hybridization of two nucleic acid sequences, e.g., probe and target sequences, although the sequences are not completely complementary. That is, a "sufficiently complementary" sequence that hybridizes to another sequence by hydrogen bonding between a subset series of complementary nucleotides by using standard base pairing (e.g., G:C, A:T or A:U), although the two sequences may contain one or more residues (including abasic positions) that are not complementary so long as the entire sequences in appropriate hybridization conditions to form a stable hybridization complex. Sufficiently complementary sequences are preferably at least about 80%, more preferably at least about 90%, and most preferably completely complementary in the sequences that hybridize together. Appropriate hybridization conditions are well known to those skilled in the art, can be predicted based on sequence composition, or can be determined empirically by using routine testing (e.g., Sambrook et al., *Molecular Cloning, A Laboratory Manual*, $2^{nd}$ ed. at §§ 1.90-1.91, 7.37-7.57, 9.47-9.51 and 11.47-11.57, particularly §§ 9.50-9.51, 11.12-11.13, 11.45-11.47 and 11.55-11.57).

"Consisting essentially of" means that additional component(s), composition(s) or method step(s) that do not materially change the basic and novel characteristics of the compositions and methods described herein may be included in those compositions or methods. Such characteristics include the ability to detect an influenza virus A or influenza virus B nucleic acid sequence present in a sample with specificity that distinguishes the influenza virus nucleic acid from at least 50 other known respiratory pathogens, preferably at a sensitivity that detects at least 1.7 to 2.7 log copies of the influenza virus, within about 45 min from the beginning of an amplification reaction that makes amplified viral sequences that are detected.

Unless defined otherwise, all scientific and technical terms used herein have the same meaning as commonly understood by those skilled in the relevant art. General definitions may be found in technical books relevant to the art of molecular biology, e.g., *Dictionary of Microbiology and Molecular Biology*, 2nd ed. (Singleton et al., 1994, John Wiley & Sons, New York, N.Y.) or *The Harper Collins Dictionary of Biology* (Hale & Marham, 1991, Harper Perennial, New York, N.Y.). Unless mentioned otherwise, techniques employed or contemplated herein are standard methodologies well known to one of ordinary skill in the art. The examples included herein illustrate some preferred embodiments.

Compositions that include nucleic acid oligomers that function in target capture, amplification, and detection of nucleic acids and methods for detecting human influenza virus A ("FluA") and influenza virus B ("FluB") nucleic acid present in a biological sample are disclosed herein. To select target sequences appropriate for use in the tests to detect influenza virus A, known influenza virus A RNA or DNA sequences that encode a matrix protein (MP1), including partial or complementary sequences (available at publicly accessible databases, e.g., GenBank), were aligned by matching regions of identical or similar sequences and compared. To select target sequences appropriate for use in the tests to detect influenza virus B, known influenza virus B RNA or DNA sequences that encode a non-structural protein (NS1), including partial or complementary sequences (available at publicly accessible databases, e.g., GenBank) were aligned by matching regions of identical or similar sequences and compared. Although sequence comparisons may be facilitated by use of computer-performed algorithms, one of ordinary skill can perform the comparisons manually and visually. Portions of sequences for each viral target that contained relatively few sequence changes between the compared individual viral sequences were chosen as a basis for designing synthetic oligomers for use in the methods described herein. Oligonucleotide sequences for detecting the FluA target are shown in Table 1, and sequences for detecting the FluB target are shown in Table 2. In both tables, a preferred function is included for each sequence, and for sequences identified as promoter primers as the preferred function, the sequences include a 5' T7 bacteriophage promoter sequence (underlined, consisting of SEQ ID NO:19 or SEQ ID NO:20) from which a T7 RNA polymerase can initiate transcription under appropriate conditions. Those skilled in the art will appreciate that another 5' promoter sequence may be substituted for the underlined T7 promoter sequence, which would then function with the appropriate RNA polymerase for the chosen other promoter sequence, to make an equivalent promoter primer oligonucleotide. Oligomers having the same target-specific sequences as the promoter primers but without the promoter sequence are also shown (SEQ ID Nos. 13-18 and 41-43) which are capable of functioning as primers in amplification systems that do not use promoter primers. Those skilled in the art will recognize that oligomers identified as having a preferred function in target capture have target-specific portions (shown in SEQ ID Nos. 3, 4, 36, and 37) and optionally include tail portions ($T_3A_{30}$ shown in SEQ ID Nos. 5, 6, 34, and 35) which may be deleted or substituted with other sequences or binding moieties.

TABLE 1

Oligomer Sequences Specific for Influenza virus A Detection Assays

| SEQ ID | Sequence | Preferred Function |
|---|---|---|
| 3 | gaggcccatgcaactggcaagtgcac | target capture |
| 4 | gaatccacaatatcaagtgcaagatccc | target capture |
| 5 | gaggcccatgcaactggcaagtgcacttt(a)$_{30}$ | target capture |
| 6 | gaatccacaatatcaagtgcaagatcccttt(a)$_{30}$ | target capture |
| 7 | <u>aatttatacgactcactatagggaga</u>agggcattttggacaaakcgtct | promoter primer |
| 8 | <u>aatttatacgactcactatagggaga</u>agggcattttggacaaagcgtct | promoter primer |
| 9 | <u>aatttaatacgactcactataggaga</u>agggcattttggacaaakcgtc | promoter primer |
| 10 | <u>aatttaatacgactcactatagggaga</u>agggcattttggacaaagcgtc | promoter primer |
| 11 | <u>aatttaatacgactcactatagggaga</u>agggcattttggacaaakcgt | promoter primer |
| 12 | <u>aatttaatacgactcactatagggaga</u>agggcattttggacaaagcgt | promoter primer |
| 21 | catggartggctaaagacaa | primer |
| 22 | catggartggctaaagacaaga | primer |
| 23 | gtrttcacgctcaccgtgc | primer |
| 24 | catggartggctaaagacaagacc | primer |
| 25 | caccgugcccagugagc | probe |
| 26 | gcccagugagcgagga | probe |

TABLE 1-continued

Oligomer Sequences Specific for Influenza virus A Detection Assays

| SEQ ID | Sequence | Preferred Function |
|---|---|---|
| 27 | cgaggacugcagcguag | probe |
| 28 | ggcucgugcccagugagcgagggagcc | probe |
| 29 | gugcccagugagcgaggacugcggcac | probe |
| 30 | ggcuccagugagcgaggacugcagagcc | probe |
| 31 | ggcucugagcgaggacugcagcgagcc | probe |

TABLE 2

Oligomer Sequences Specific for Influenza virus B Detection Assays

| SEQ ID | Sequence | Preferred Function |
|---|---|---|
| 34 | gucuugaccagggguagucaaggttt(a)$_{30}$ | target capture |
| 35 | ggcucaaacccuucaauuccttt(a)$_{30}$ | target capture |
| 38 | aatttaatacgactcactatagggagacggtgctcttgaccaaattgg | promoter primer |
| 39 | aatttaatacgactcactatagggagacggtgctcttgaccaaatt | promoter primer |
| 40 | aatttaatacgactcactatagggagacggtgctcttgaccaaattg | promoter primer |
| 44 | tcctcaactcactcttcga | primer |
| 45 | tcctcaactcactcttcgagcg | primer |
| 46 | tcctcaactcactcttcgagc | primer |
| 47 | gaaggacattcaaagcc | primer |
| 48 | gccaauucgagcagcug | probe |
| 49 | gagcagcugaaacugcg | probe |
| 50 | gcagcugaaacugcggugg | probe |
| 51 | cgcacgcagcugaaacugcggugcg | probe |
| 52 | ccagcgccaauucgagcagcugg | probe |
| 53 | cgguggcugaaacugcgguggcaccg | probe |
| 54 | ggcucuucgagcagcugaaacuggagcc | probe |
| 55 | ggcucucgagcagcugaaacuggagcc | probe |
| 56 | ggcucauucgagcagcugaaacugugagcc | probe |
| 57 | ggcucguucgagcagcugaaacugcgagcc | probe |
| 58 | cgcagucgagcagcugaaacugcg | probe |

Although sequences are shown in Tables 1 and 2 as DNA, RNA or mixed DNA/RNA sequences, the sequences are meant to include the corresponding DNA or RNA sequences, and their completely complementary DNA or RNA sequences. Preferred embodiments of oligomers may include one or more modified residues affecting the backbone structure (e.g., 2'-methoxy substituted RNA groups), or one or more LNA monomers, preferably at 5' residues of a primer oligomer, or may include a non-nucleotide linker to attach a label to the oligomer. For example, oligomers that function as probes for RNA targets may be synthesized with 2'-methoxy substituted RNA groups to promote more stable hybridization between probe and target sequences. Embodiments include oligomers of SEQ ID Nos. 25-27 synthesized with 2'-methoxy substituted RNA groups and having a non-nucleotide linker (as described in U.S. Pat. No. 5,585,481) between residues 6 and 7 of SEQ ID NO:25, between residues 7 and 8 of SEQ ID Nos. 26 and 50, between residues 8 and 9 of SEQ ID Nos. 26 and 27, and between residues 9 and 10 of SEQ ID Nos. 48 and 49. Other embodiments include oligomers of SEQ ID Nos. 44 and 45 synthesized with LNA at 5' residues 1 to 3, and an oligomer of SEQ ID NO:46 synthesized with LNA at 5' residues 1 to 4.

Preferred embodiments of target capture oligomers include a target-specific sequence that binds specifically to the FluA or FluB target nucleic acid and a covalently linked "tail" sequence ($T_3A_{30}$ in SEQ ID Nos. 5, 6, 34 and 35) used in capturing the hybridization complex containing the target nucleic acid to an immobilized sequence on a solid support. Preferred embodiments of capture oligomers include at least one 2' methoxy linkage. Embodiments of capture oligomers may include the target-specific sequence that binds to a FluA or FluB genomic sequence attached to another binding moiety, e.g., a biotinylated sequence that binds specifically to immobilized avidin or streptavidin. The tail sequence or binding moiety binds to an immobilized probe (e.g., complementary sequence or avidin) to capture the hybridized target and separate it from other sample components by separating the solid support from the mixture.

Primer sequences, including promoter primer sequences, bind specifically to the target nucleic acid or its complementary sequence and may contain additional sequences that are not target-specific, e.g., the promoter sequence in a promoter primer. A target-specific sequence, with or without an attached promoter sequence, may serve as an amplification oligomer in a variety of in vitro amplification processes. Embodiments of the FluA and FluB assays may use amplification methods that require multiple cycling reaction temperatures, such as PCR (U.S. Pat. Nos. 4,683,195, 4,683,202, and 4,800,159), or may be substantially isothermal as in transcription associated amplification methods, such as TMA or NASBA (e.g., U.S. Pat. Nos. 5,399,491, 5,480,784, 5,824,518, 5,888,779, 5,786,183, 5,437,990, 5,130,238, 4,868,105, and 5,124,246, and PCT Nos. WO 8801302 and WO 8810315). Preferred embodiments of the FluA and FluB assays use PCR-based or TMA-based amplification systems that are detected during the amplification process (i.e., real time detection) by including probes that emit distinguishable fluorescent signals when the probe is bound to the intended target sequence made during the amplification process. Preferred probes for real time detection include those referred to as "molecular beacon" or "molecular switch" probes (e.g., U.S. Pat. Nos. 5,118,801 and 5,312,728, Lizardi et al., U.S. Pat. Nos. 5,925,517 and 6,150,097, Tyagi et al., Giesendorf et al., 1998, Clin. Chem. 44(3):482-6) and "molecular torch" probes (e.g., U.S. Pat. Nos. 6,835,542 and 6,849,412, Becker et al.). Generally, such probes include a reporter dye attached to one end of the probe oligomer (e.g., FAM™, TET™, JOE™, VIC™) and a quencher compound (e.g., TAMRA™ or non-fluorescent quencher) attached to the other end of the probe oligomer, and signal production depends on whether the two ends with their attached compounds are in close proximity or separated.

The assay to detect influenza virus in a sample includes the steps of amplifying a target region in the target influenza virus nucleic acid contained in a sample by using amplification oligomers or primers specific for the intended target region, and detecting the amplified nucleic acid by hybridizing it to a probe sequence. Preferred assays use a transcription-associated amplification reaction and detection is during the amplification reaction. For detection, the amplified nucleic acid may be labeled and bound to an unlabeled probe, but preferred embodiments bind a labeled probe to the amplified nucleic acid. A preferred embodiment for real-time detection uses a labeled probe that is detected in a homogeneous system.

Generally, the target influenza virus nucleic acid is separated from other sample components before the amplification step. This may be done by capturing the influenza virus nucleic acid by using a target-specific capture oligomer that binds specifically to the target influenza virus nucleic acid, or by using non-specific methods of purifying nucleic acid from a sample (e.g., U.S. Pat. Nos. 5,234,809, 5,705,628, 6,534,262 and 6,939,672). Preferred embodiments use uses a target-specific capture oligomer in a capturing step (U.S. Pat. Nos. 6,110,678, 6,280,952 and 6,534,273). Embodiments of capture probes include those specific for influenza virus A nucleic acid (SEQ ID Nos. 3 to 6), and those specific for influenza virus B nucleic acid (SEQ ID Nos. 34 to 37). Embodiments of SEQ ID Nos. 5, 6, 34, and 35 include a $dT_3A_{30}$ tail portion for hybridization to a complementary immobilized sequence, whereas embodiments of SEQ ID Nos. 3, 4, 36 and 37 are used in conjunction with another ligand that is a member of a binding pair (e.g., biotinylated DNA to bind to immobilized avidin or streptavidin). The complex the capture probe, its target influenza virus nucleic acid, and an immobilized binding partner or probe facilitate separation of the influenza virus nucleic acid from other sample components, and optional washing steps may be used to further purify the captured viral nucleic acid.

Amplifying the influenza virus target region using two primers may be accomplished using a variety of known nucleic acid amplification reactions, but preferably uses a transcription-associated amplification reaction, such as TMA (described in detail in U.S. Pat. Nos. 5,399,491 and 5,554,516). A TMA-based assay produces many RNA transcripts (amplicons) from a single copy of target nucleic acid, and the amplicons are detected to indicate the presence of the target influenza virus in the sample. Briefly, in TMA-based assays, a promoter-primer hybridizes specifically to the target sequence and reverse transcriptase (RT) that includes RnaseH activity creates a first strand cDNA by extension from the 3' end of the promoter-primer and digests the template strand. The cDNA is then bound by a second primer and a new strand of DNA is synthesized from the end of the second primer using RT to create a double-stranded DNA (dsDNA) containing a functional promoter sequence. RNA polymerase specific for that promoter binds to the promoter sequence and multiple RNA transcripts are produced, which each can act as a template for additional sequence replication using the same steps used for the initial template. Thus, large amounts of single-stranded amplified product are made using substantially isothermal reaction conditions.

Another embodiment of the influenza virus assay uses PCR amplification (U.S. Pat. Nos. 4,683,195, 4,683,202, and 4,800,159, Mullis et al.) to produce multiple DNA strands by using thermocycling reactions that separate dsDNA and primers specific for portions of the separated strands to make additional dsDNA molecules by using a DNA polymerase. Well known variations of the basic PCR method may also be used, e.g., reverse-transcriptase PCR that uses RT to produce a cDNA from an RNA template, and then the DNA is amplified by PCR cycles, or PCR coupled with real-time detection, both of which are sometimes referred to as RT-PCR (e.g., TaqMan One-Step RT-PCR kits, Applied Biosystems, Inc., Foster City, Calif.).

Embodiments of amplification oligomers specific for influenza virus A nucleic acid include promoter primers of SEQ ID Nos. 7 to 12, target-specific sequences of SEQ ID Nos. 13 to 18 which are contained in the promoter primers, and SEQ ID Nos. 19 to 24. A preferred composition includes a mixture of oligomers of SEQ ID NO:7 and SEQ ID NO:21, where SEQ ID NO:21 has LNA residues at positions 1 to 3, which composition is useful for TMA-based amplification of the influenza virus A target region of SEQ ID NO:1.

Embodiments of amplification oligomers specific for influenza virus B nucleic acid include promoter primers of SEQ ID Nos. 38 to 40, target-specific sequences of SEQ ID Nos. 41 to 43 which are contained in the promoter primers, and SEQ ID Nos. 44 to 47. A preferred composition includes a mixture of oligomers of SEQ ID NO:39 and SEQ ID NO:44, where SEQ ID NO:44 includes LNA residues at positions 1 to 3, which composition is useful for TMA-based amplification of the influenza virus B target region of SEQ ID NO:32.

The methods for detecting influenza virus nucleic acid include a detecting step that uses at least one probe that binds specifically to the amplified influenza virus product (RNA or DNA amplicons). Preferably, the probe is labeled and produces a signal detected in a homogeneous system, i.e., without separation of bound probe from unbound probe. Preferred probes are labeled with an acridinium ester (AE) compound from which a chemiluminescent signal is produced and detected in a homogeneous system (substantially as described in detail in U.S. Pat. Nos. 5,283,174, 5,656,744, and 5,658,737). Other preferred probes are labeled with a fluorescent compound which emits a detectable signal only when the probe is bound to its target, e.g., molecular switch, beacon, or torch probes. Preferred probes for specific detection of influenza virus A sequences include oligomers of SEQ ID Nos. 25 to 27, preferably AE-labeled between residues 6 and 7 for SEQ ID NO:25, between residues 7 and 8 or 8 and 9 for SEQ ID NO:26, and between residues 8 and 9 for SEQ ID NO:27. Other preferred probes for specific detection of influenza virus A sequences include fluorescent compound-labeled oligomers of SEQ ID Nos. 28 to 31. Preferred probes for specific detection of influenza virus B sequnces include oligomers of SEQ ID Nos. 48 to 50, preferably AE-labeled between residues 9 and 10 for SEQ ID Nos. 48 and 49, and between residues 7 and 8 for SEQ ID NO:50. Other preferred probes for specific detection of influenza virus A sequnces include fluorescent compound-labeled oligomers of SEQ ID Nos. 51 to 58.

Preferred embodiments of assays for detection of influenza virus A or B nucleic acid include an internal control (IC) nucleic acid that is amplified and detected by using IC-specific primers and probe in the same reaction mixtures used for influenza virus nucleic acid amplification and detection. Amplification and detection the IC-specific sequence demonstrates that assay reagents and conditions were properly used even when no influenza virus-specific signal is detected for a tested sample (i.e., negative samples). The IC may be used as an internal calibrator for the assay that provides a quantitative result. A preferred IC embodiment is a randomized sequence derived from a naturally occurring source that is not an influenza virus (e.g., HIV). An preferred IC is SEQ ID NO:65 or its RNA transcript, and preferred embodiments of primers for amplification of this IC include those of SEQ ID Nos. 61, 62, 64, 66, and 67. Probes for detection of IC amplicons include any oligomer of at least ten residues that hybridizes specifically to a contiguous sequence contained in SEQ ID NO:65 or its complement (DNA or RNA) under assay conditions described herein. A preferred IC-specific probe is exemplified by an oligomer of SEQ ID NO:63 labeled with a fluorescent compound at one end and a quencher at the other end. In preferred embodiments that include an IC in an assay, the IC is treated throughout the assay similar to the intended analyte. For example, when a target capture step is used for purification of the influenza virus nucleic acid target in a sample, the target capture step includes a capture oligomer specific for the IC to purify the IC from a mixture that includes the target influenza virus nucleic acid and other sample components. Preferred embodiments of capture oligomers specific for the IC of SEQ ID NO:65 include those of SEQ ID Nos. 59 and 60.

In general, methods used to demonstrate amplification and detection of influenza virus A or B nucleic acid by using the compositions described herein involved the following steps. Influenza viral RNA was separated from other sample components by using a method that attaches the target influenza virus nucleic acid to a solid support that is separated from other sample components. In preferred embodiments, viral RNA was separated from other sample components by using a target-capture system that included a target-specific capture probe for the influenza viral analyte (e.g., using methods steps described in U.S. Pat. Nos. 6,110,678, 6,280,952 and 6,534,273), or a non-specific method for separation of nucleic acids was used (U.S. Pat. No. 5,234,809). Non-specific separation of viral RNA from other sample components was performed by adhering nucleic acids reversibly to a solid support, followed by washing and elution of the adhered nucleic acids into a substantially aqueous solution (e.g., using a QIAAMP™ Viral RNA Mini kit, Qiagen Inc.). Isolated influenza virus nucleic acid was amplified for specific target sequences contained the genome by using TMA or PCR amplification, and the amplification products were detected after completion of the amplification reaction or during amplification (i.e., real-time detection). For real-time detection, a fluorophore-labeled probe (e.g., molecular beacon) was used that emits a detectable signal only when the probe is hybridized to its target sequence, and fluorescence was detected using standard fluorometry. Generally, assays detected two different probes (with different 5' fluorophores): an influenza virus-specific probe and an IC-specific probe. Fluorescence was detected by using a system that incubates the reactions and detects fluorescence at different wavelengths at time intervals during the reaction (e.g., DNA Engine OPTICON™ 2 system or CHROMO4™ Real-Time PCR Detector, Bio-Rad Laboratories, Inc., Hercules, Calif.). Real-time detected fluorescent signals in each channel were analyzed using standard methods. For example, detected signals were normalized to generate a best-fit curve to the data points for each reaction (relative fluorescence vs. time) and results were reported as the time of emergence when the signal met or exceeded a pre-set level.

For comparison with TMA-based assays, real-time reverse-transcriptase PCR-based assays (RT-PCR) were performed by using 0.9 pmol/µl of primers (SEQ ID NO:68 and SEQ ID NO:69 for influenza virus A, or SEQ ID NO:71 and SEQ ID NO:72 for influenza virus B) and 0.2 pmol/µl of probe (SEQ ID NO:70 for influenza virus A and SEQ ID NO:73 for influenza virus B) in a 50 µl reaction that included standard PCR reaction components (provided by TAQMAN® One-Step RT-PCR Master Mix Reagents Kit, Applied Biosystems, Inc.). Incubation was performed using: 48° C. for 30 min, 95° C. for 10 min, then 45 cycles of 95° C. for 15 sec and cooling, and finally 60° C. for 1 min. Amplification and detection of the molecular beacon probe hybridized to its target amplified product were performed by using an open channel system (CHROMO4™, Bio-Rad Laboratories, Inc.) for real-time fluorescence detection, with fluorescent signal readings taken at each of the 45 cycles. Real-time fluorescence signals were analyzed and detection of the analytes calculated from the fluorescence emergence curves by using standard methods.

Real-time TMA-based assays typically were performed in reaction mixture that contained the analyte nucleic acid, amplification reagent (APTIMA™ reagent, Gen-Probe Incorporated, San Diego, Calif.), a T7 promoter primer that included (9 pmol/reaction), a second primer without a promoter (15 pmol/reaction), and a molecular beacon probe (0.2-0.3 pmol/reaction) for amplicon detection, in a 40 µl reaction (in a well of a standard 96-well plate, covered with a layer of inert oil or sealing device to prevent evaporation). The mixture of target nucleic acid, primers, and probe was incubated at 60° C. for 10 min, cooled at 42° C. for 5 min, and then enzyme reagent containing RT and T7 RNA polymerase was added, the mixture was mixed (e.g., 30 sec vortex) and then incubated at 42° C. for 75-100 min for isothermal amplification during which detection of fluorescence was performed every 3 sec. Amplification and detection steps were performed using an incubation and open channel fluorimeter (CHROMO4™, Bio-Rad Laboratories, Inc.) for real-time two-color fluorescence detection. Generally, the assays included an IC, as described above, i.e., a reaction mixture included primers and probe for the target influenza virus nucleic acid and IC-specific primers and probe, each probe labeled with a separately detectable 5' fluorophore. Real-time fluorescence signals were analyzed and a detection signal (time of emergence) was calculated. Time of emergence was calculated, e.g., by using a method that analyzes the detected signals (relative fluorescence units or RFU) relative to the signal detection times (RFU(t) data points) to determine a time of emergence ("T-time"), which is the time at which a RFU(t) data point reaches a predefined threshold value (described in detail in U.S. application 60/659,874, Scalese et al., filed Mar. 10, 2005). Briefly, RFU(t) data is treated to subtract background signal ("noise" level) and curves (RFU vs time) are normalized to optimize curve fit for data between predetermined minimum and maximum points. In general, samples that contain a higher analyte concentration result in a steeper curve slope and an earlier time of emergence. In the examples described herein, samples often contained known amounts of the target influenza virus nucleic acid (influenza virus A or B RNA, expressed as "log copies" per reaction) and the average (mean) time of emergence (average Ttime) was determined for replicate tests performed identically. Average times of emergence were compared to determine the relative efficiencies of the different assay conditions, e.g., to compare for a single known amount of analyte, the time of emergence detected by using a PCR-based assay compared to using a TMA-based assay. For TMA-based assays that included an IC, the IC was a known amount of RNA transcripts made in vitro from SEQ ID NO:65 that was amplified by using IC-specific primers in the same reaction as for amplification of the target influenza virus nucleic acid. Generally, for influenza A virus assays, IC-specific primers were SEQ ID NO:61 (0.5 pmol/reaction) and SEQ ID NO:62 (15 pmol/reaction), and for influenza virus B assays, IC-specific primers were SEQ ID NO:64 (0.5 pmol/reaction) and SEQ ID NO:62 (15 pmol/reaction), with a IC-specific detection probe of SEQ ID NO:63 (0.75 pmol/reaction) for both assays.

TMA-based FluA and FluB assays with real-time detection resulted in 100% specificity for their respective influenza virus targets when tested against other respiratory viruses, microbes (bacteria and fungi) commonly associated with oral or respiratory flora or infections, and several human influenza virus subtypes. Tests performed on clinical samples that had been collected during influenza seasons over a four-year period demonstrated 100% agreement in sensitivity and specificity when the TMA-based and PCR-based assays described herein were compared. TMA-based assays with real-time detection were advantageous positive detection results that indicated the presence of the influenza virus in the sample were obtained in a shorter time than required for the real-time PCR-based assay to detect the viral nucleic acids. For example, TMA-based assays with real-time detection generally provided positive results in less than 45 min from the start of the amplification reaction, whereas PCR-based assays with real-time detection typically required up to two hours or more to provide positive results.

Unless otherwise specified, reagents commonly used in the TMA-based assays described herein include the following. Sample transport reagent: 110 mM lithium lauryl sulfate (LLS), 15 mM $NaH_2PO_4$, 15 mM $Na_2HPO_4$, 1 mM EDTA, 1 mM EGTA, pH 6.7. Lysis buffer: 790 mM HEPES, 230 mM succinic acid, 10% (w/v) LLS, and 680 mM LiOH monohydrate. Target Capture Reagent (TCR): 250 mM HEPES, 1.88 M LiCl, 310 mM LiOH, 100 mM EDTA, pH 6.4, and 250 µg/ml of paramagnetic particles (0.7-1.05µ particles, Sera-Mag™ MG-CM) with $(dT)_{14}$ oligomers covalently bound thereto. Wash Solution: 10 mM HEPES, 150 mM NaCl, 6.5 mM NaOH, 1 mM EDTA, 0.3% (v/v) ethanol, 0.02% (w/v) methylparaben, 0.01% (w/v) propylparaben, and 0.1% (w/v) sodium lauryl sulfate, pH 7.5. Amplification reagent: a concentrated solution containing 125 mM HEPES, 26.7 mM rATP, 33.3 mM rGTP, 5 mM each of rCTP and UTP, 1.33 mM each of dATP, dCTP, dGTP and dTTP, 8% (w/v) trehalose, pH 7.7, to which primers and probes may be added. TMA Enzymes: per reaction about 90 U/µl of MMLV reverse transcriptase (RT) and about 20 U/µl of T7 RNA polymerase per reaction (where 1 U of RT incorporates 1 nmol of dTTP in 10 min at 37° C. using 200-400 µM oligo-dT-primed polyA-template, and 1 U of T7 RNA polymerase incorporates 1 nmol of ATP into RNA in 1 hr at 37° C. using a T7 promoter in DNA template). Probe Reagent for AE-labeled probes: a solution of (a) 100 mM Li-succinate, 3% (w/v) LLS, 10 mM mercaptoethanesulfonate (MES), and 3% (w/v) polyvinylpyrrolidon, or (b) 100 mM Li-succinate, 0.1% (w/v) LLS, and 10 mM MES. Hybridization Reagent: (C-type) 100 mM succinic acid, 2% (w/v) LLS, 100 mM LiOH, 15 mM aldrithiol-2, 1.2 M LiCl, 20 mM EDTA, and 3.0% (v/v) ethanol, pH 4.7. Selection Reagent: 600 mM boric acid, 182.5 mM NaOH, 1% (v/v) octoxynol (TRITON® X-100), pH 8.5 to 9.2, to hydrolyze AE labels on unbound oligomers. Detection Reagents for AE labels are Detect Reagent I: 1 mM nitric acid and 32 mM $H_2O_2$, and Detect Reagent II: 1.5 M NaOH (see U.S. Pat. Nos. 5,283,174, 5,656,744, and 5,658,737).

EXAMPLE 1

TMA-Based Assays for Amplification and Detection of Influenza Viruses

This example demonstrates a TMA-based assay for influenza virus type A detection (FluA assay) and a TMA-based assay for influenza virus type B detection (FluB assay), both using an internal control (IC) that is amplified and detected in the same assay conditions.

The TMA-based FluA assay used primers of SEQ ID NO:8 (9 pmol/reaction) and SEQ ID NO:21 (15 pmol/reaction) and a fluorophore-labeled probe of SEQ ID NO:29 (0.32 pmol/reaction) in a TMA reaction performed substantially as described above using varying amounts of influenza virus A target (RNA transcript of SEQ ID NO:1, at 0 to 6.7 log copies per reaction). Reactions were performed with or without IC components (primers of SEQ ID Nos. 61 and 62, probe of SEQ ID NO:63, and IC target RNA transcripts of SEQ ID NO:65 at 0 or 2.3 log copies per reaction). Six replicates of each reaction were performed, each reaction in a well of a standard 96-well plate, using 30 µl of amplification reagent containing the appropriate target oligonucleotides, incubated at 60° C. for 10 min and at 42° C. for 5 min, and then TMA enzymes were added to each reaction in enzyme reagent (10 µl per reaction), reaction were mixed (30 sec vortex), followed by amplification incubation for 45-60 min at 42° C.

during which the fluorescent probe signal was detected at time intervals as described above (in a CHROMO4® instrument). Results of the tests are shown in Table 3, expressed as average time of emergence of signal for the influenza virus A analyte (with standard deviation (SD) where calculated). Negative control samples (no influenza virus A target included) provided the background noise signal for calculation of the emergence times of the positive samples. The results show that the dynamic range of the assay for detection of the influenza virus A target was from 1.7 to 6.7 log copies of the viral target, and the IC was detected over the viral target titration range (up to 6.7 log copies).

TABLE 3

Real-Time Detection of Influenza Virus A
During In Vitro Nucleic Acid Amplification

| Influenza virus A target | Average Emergence Time ± SD (min) | |
|---|---|---|
| (log copies) | With IC (2.3 log copies) | Without IC |
| 1.70 | 31.5 | 24.2 ± 0.51 |
| 2.70 | 28.9 ± 1.34 | 21.3 ± 0.38 |
| 3.70 | 25.6 ± 1.04 | 19.0 ± 0.45 |
| 4.70 | 19.8 ± 0.33 | 17.0 ± 0.07 |
| 5.70 | 16.6 ± 0.65 | 15.2 ± 0.18 |
| 6.70 | 14.6 ± 0.23 | 13.5 ± 0.26 |

Separate TMA-based assays were performed using substantially the same procedure described above, but with 2.7 or 3.7 log copies of influenza virus A target (transcripts of SEQ ID NO:1) amplified by using different promoter primers (SEQ ID Nos. 8, 9, 10 and 12, each tested separately at 9 pmol/reaction) with a second primer of SEQ ID NO:21 (15 pmol/reaction), and amplicons detected by using a fluorophore-labeled probe of SEQ ID NO:29 (8 pmol/reaction). Similar results for positive signals were obtained in these tests using the different combinations of primers although some combinations were more efficient at amplification as determined by the shorter times of signal emergence. For primers of SEQ ID Nos. 8 and 21, the emergence times were 20.9 to 25.8 min, for primers of SEQ ID Nos. 9 and 21, the emergence times were 30.4 to 34.8 min, for the primers of SEQ ID Nos. 10 and 21, the emergence times were 19.4 to 27.9 min, and for the primers of SEQ ID Nos. 12 and 21, the emergence times were 19.8 to 25.8 min.

TMA-based FluB assays were performed using similar conditions but influenza virus B-specific primers and probes. In one embodiment, primers of SEQ ID NO:39 (9 pmol/reaction) and SEQ ID NO:44 (15 pmol/reaction) were used to amplify varying amounts of the influenza virus B target (RNA transcript of SEQ ID NO:32, at 0 to 7.7 log copies per reaction), and amplicons were detected using fluorophore-labeled probe of SEQ ID NO:52 (8 pmol/reaction). Reactions were performed substantially as described above, with or without IC components (primers of SEQ ID Nos. 64 and 62, probe of SEQ ID NO:63, and IC targets that were RNA transcripts of SEQ ID NO:65 at 0 or 2.3 log copies per reaction). Results of these FluB assays are shown in Table 4, expressed as average time of signal emergence for the influenza virus B analyte (with standard deviation (SD) where calculated). Results of negative control samples (no influenza virus target) served as the background noise signal for calculation of the emergence times of the positive samples. These results show that the dynamic range of the FluB assay was from 1.7 to 7.7 log copies of influenza virus B target and the IC was detected up to 5.7 log copies of the influenza virus B target per reaction.

TABLE 4

Real-Time Detection of Influenza Virus B Nucleic
During In Vitro Nucleic Acid Amplification

| Influenza virus B target | Average Emergence Time ± SD (min) | |
|---|---|---|
| (log copies) | With IC (2.3 log copies) | Without IC |
| 1.70 | 38.8 ± 0.37 | 41.0 ± 2.62 |
| 2.70 | 35.9 ± 0.27 | 36.1 ± 1.76 |
| 3.70 | 31.7 ± 1.70 | 31.8 ± 1.26 |
| 4.70 | 27.6 ± 1.07 | 28.6 ± 0.63 |
| 5.70 | 24.5 ± 0.85 | 25.5 ± 0.27 |
| 6.70 | 20.6 ± 0.12 | 21.0 ± 0.73 |
| 7.7 | 17.2 ± 0.19 | 16.9 ± 0.18 |

Separate TMA-based FluB assays were performed using conditions like those described above, but detected with different fluorophore-labeled probes of SEQ ID Nos. 52, 55 and 58, which provided similar results. In these TMA-based FluB assays, the primers were SEQ ID NO:39 (3 pmol/reaction) and SEQ ID NO:44 (15 pmol/reaction) to amplify the influenza virus B RNA target at 8 log copies per reaction. Each of the detection probes (about 0.3 pmol/reaction) were tested separately in seven replicate amplification and detection assays as described above. For these assays, the average emergence times were: 14.0±0.16 min for the SEQ ID NO:52 probe, 10.7±0.22 min for the SEQ ID NO:55 probe, and 12.0±0.33 min for the SEQ ID NO:58 probe. In separate experiments performed using similar conditions but with fluorophore-labeled probes of SEQ ID Nos. 51, 52, 53, 56, and 57, and lower amounts of the influenza virus B target RNA (4.3 log copies per reaction), the average emergence times were: 24.9±0.12 min for the SEQ ID NO:56 probe, 25.8±0.05 min for the SEQ ID NO:57 probe, 26.5±0.30 min for the SEQ ID NO:52 probe, 26.6±0.59 min for the SEQ ID NO:53 probe, and 31.8±0.48 min for the SEQ ID NO:51 probe.

In similar tests, the TMA-based FluA and FluB assays were performed using different combinations of IC primers. In the FluA assays, influenza virus A-specific primers of SEQ ID Nos. 9 and 21 amplified the influenza virus A RNA (transcript of SEQ ID NO:1 at 3.7 log copies per reaction), and amplicons were detected using a fluorophore-labeled influenza virus A-specific probe of SEQ ID NO:29. In the FluB assays, influenza virus B-specific primers of SEQ ID Nos. 39 and 44 amplified the influenza virus B RNA (transcripts of SEQ ID NO:32 at 4.7 log copies per reaction), and amplicons were detected using a fluorophore-labeled probe of SEQ ID NO:48. For both the FluA and FluB assays, different combinations of IC-specific oligomers were used to amplify the IC (RNA transcript of SEQ ID NO:65 at 2.3 log copies per reaction): primer of SEQ ID NO:62 (10 pmol/reaction) was combined with about 0.5 pmol/reaction of primer of SEQ ID Nos. 61, 64, 66 or 67, and then the IC amplicons were detected in all reactions by using a fluorophore-labeled probe of SEQ ID NO:63. The results of these tests showed that all of the combinations of IC-specific primers could be used in the FluA and FluB assays without interfering with detection of the respective influenza viral target for the assay, but the promoter primer of SEQ ID NO:61 was optimal for the FluA assay whereas the promoter primer of SEQ ID NO:64 was optimal for the FluB assay.

EXAMPLE 2

Specificity of TMA-Based FluA and FluB Assays

This example demonstrates the specificity of the TMA-based FluA and FluB assays, which specifically detected the intended viral target for each test and did not provide a positive signal when samples contained other bacterial or viral agents commonly found in normal human oral flora or respiratory infections. The TMA-based FluA and FluB assays were performed substantially as described in Example 1 except that the tested samples included known microbes or viruses and did not contain influenza virus A or influenza virus B nucleic acid (except for positive controls). That is, the assays provided negative results showing that the assays did not cross-react with other microbial or viral nucleic acids. An IC RNA was included in all of the tests to demonstrate that the assay conditions and amplification and detection steps had been performed appropriately to detect the IC target (or any cross-reactive target) in the sample.

Each sample containing a known virus was tested independently using the TMA-based FluA test with IC and the FluB test with the same IC. Separate FluA and FluB assays were performed simultaneously under the same conditions using positive control samples that contained influenza virus A or influenza virus B targets. Positive controls included four sources of influenza virus A nucleic acid and two sources of influenza virus B nucleic acid, each tested individually at $10^5$ and $10^2$ copies per reaction (with American Type Culture Collection (ATCC) accession numbers provided below). Positive control samples for influenza virus A included: isolates of A/Port Chalmers/1/73(H3N2) (ATCC VR-810), A/Mal/302/54(H1N1) (ATCC VR-98), and A/Hong Kong/8/68(H3N2) (ATCC VR-544), and in vitro RNA transcripts of Flu A/Beijing(H1N1) (an isolate from the Center for Disease Control (CDC), Atlanta, Ga.). Positive control samples for influenza virus B included: in vitro RNA transcripts of B/Maryland/1/59 (ATCC VR-296) and isolate B/Lee/40 (ATCC VR-101).

The TMA-based FluA assay was performed by using primers of SEQ ID NO:8 (9 pmol/reaction) and SEQ ID NO:21 with LNA for residues 1 to 3 (15 pmol/reaction), and a molecular beacon probe of SEQ ID NO:29 (0.267 pmol/reaction) for real-time detection of the TMA amplicons. The reactions included an IC (RNA transcripts of SEQ ID NO:65 at 200 copies/reaction) that was amplified by using primers of SEQ ID Nos. 61 and 62 (0.5 and 15 pmol/reaction, respectively), and the IC amplicons were detected in real time by using a molecular beacon probe of SEQ ID NO:63 (0.6 pmol/reaction). Additional positive controls were tested at the same time using the same conditions but using samples that contained known amounts of an influenza virus A target (RNA transcripts of SEQ ID NO:1 at 2 or 5 log copies per reaction).

The TMA-based FluB assay was performed by using primers of SEQ ID NO:39 (9 pmol/reaction) and SEQ ID NO:44 with LNA for residues 1 to 3 (15 pmol/reaction), and a molecular beacon probe of SEQ ID NO:52 (0.267-0.32 pmol/reaction) for real-time detection of TMA amplicons. The assays included an IC (RNA transcripts of SEQ ID NO:65 at 200 copies/reaction) that was amplified by using primers of SEQ ID Nos. 64 and 62 (0.5 and 15 pmol/reaction, respectively), and IC amplicons were detected in real time by using a molecular beacon probe of SEQ ID NO:63 (0.6 pmol/reaction). Positive controls were tested at the same time under the same conditions but using samples that contained a known amount of the influenza virus B target (RNA transcripts of SEQ ID NO:32 at 2 or 5 log copies per reaction).

The TMA-based FluA assay gave positive results for all tested samples that contained influenza virus A nucleic acids (average emergence time for positive signals was 13.9 min) and negative results for all control samples that contained influenza virus B nucleic acid. Similarly, the TMA-based FluB assay gave positive results for all tested samples that contained influenza virus B nucleic acids (average emergence time for positive signals was 21.9 min) and negative results for all influenza virus A control samples.

The common normal or pathogenic microbe species and isolates (with ATCC accession Nos.) that were tested in samples included: Bordetella bronchiseptica (ATCC 10580), Bordetella pertussis (ATCC 8467), Bordetella parapertussis (ATCC 15311), Burkholdia cepacia (clinical isolate), Candida albicans (ATCC 18804), Corynebacterium striatum (ATCC 6940), Escherichia coli (ATCC 29214), Enterococcus faecalis (ATCC 19433), Fluoribacter bozemanii (ATCC 33217), Fluoribacter dumoffii (ATCC 33279), Haemophilus influenzae (ATCC 33391), Haemophilus parainfluenzae (ATCC 7901), Klebsiella pneumoniae (ATCC 23357), Legionella longbeacheae (ATCC 33484), Legionella pneumophila subsp. pneumophila (type 3, ATCC 33155; type 4, ATCC 33156; type 6, ATCC 33215; and type 11, ATCC 43130), Legionella pneumophila subsp. fraseri (type 5, ATCC 33216), Moraxella cattarhalis (ATCC 25238), Pseudomonas aeruginosa (ATCC 27853 and ATCC 9027), Proteus mirabilis (ATCC 25933), Staphylococcus aureus (ATCC 25923), Staphylococcus epidermidis (ATCC 14990), Streptococcus agalactiae (GBS) (ATCC 13813), Streptococcus gordonii (viridans strep) (ATCC 33399), Streptococcus mutans (ATCC 25175), Streptococcus oralis (ATCC 10557), Streptococcus pneumoniae (ATCC 35088), Streptococcus pyogenes (GAS) (ATCC 12344), and Tatlockia micdadiae (ATCC 33204). Isolates were grown on appropriate media and then a 1 µl loop of cells was added to a microcentrifuge tube containing 150 µl of lysis reagent (a succinate buffered detergent solution), vortexed, and incubated at 95° C. for 10 min to lyse cells. Lysates were stored frozen (−20° C.) until tested, when the lysate was thawed and diluted (1:100) into water before use in the assay. For FluA and FluB assays performed using the microbial lysates, no positive responses were obtained for any of the lysates, but positive responses were detected for the internal control (IC) indicating that the assays were preformed properly with the appropriate reagents that did not cross-react with nucleic acids present in the microbial lysates. Positive controls (containing influenza virus A or B nucleic acids) gave positive results only for the intended target of the respective assay, thus demonstrating the specificity of the TMA-based FluA and FluB assays for their intended viral targets.

Assays were similarly performed to test for cross-reactivity of the TMA-based FluA or FluB assay with known non-influenza human viruses that are potential viral respiratory pathogens. Samples containing the following viruses (with ATCC accession numbers) were tested: Adenovirus 1 (strain Adenoid 71, ATCC VR-1), Adenovirus 4 (strain Rl-67, ATCC VR-4), Adenovirus 7 (strain Gomen, ATCC VR-7), Adenovirus 11 (strain Slobitski, ATCC VR-12), Adenovirus 18 (strain DC, ATCC VR-19), Adenovirus 29 (strain BP-6, ATCC VR-272), coronoavirus 229E (Group 1 type, ATCC VR-740), coronavirus OC43 (Group 2 type, ATCC VR-759), parainfluenza virus type 1 (a clinical isolate and ATCC VR-1380), parainfluenza virus type 2 (a clinical isolate and strain Greer, ATCC VR-92), parainfluenza type 3 (clinical isolate), parainfluenza 4a (strain M-25, ATCC VR-1378), rhinovirus (clinical isolate), and Respiratory Syncyntial Viruses (RSV) (a clinical isolate; strain B WV/14617/'85, ATCC VR-1400; and strain A-2, ATCC VR-1540). A total of 42 viral samples were tested, which included those listed above and separate clinical isolates collected over four years of influenza seasons. Viral RNA was extracted using a standard protocol that collects nucleic acids non-specifically on a support, washes the collected nucleic acids, and elutes the nucleic acids from the support into an aqueous solution (QIAAMP™ Viral RNA Mini Vacuum Protocol, Qiagen Inc.). All viral nucleic acids were tested immediately after extraction or stored frozen (−70 to −80° C.) until tested. For all of the non-influenza virus nucleic acids tested, both the FluA and the FluB assays gave negative results for the non-influenza viral nucleic acids but gave positive results for the IC, indicating that the assays were performed properly with appropriate components that did not cross-react with the non-influenza viral nucleic acids. All of the positive controls that contained influenza virus target nucleic acid gave the appropriate positive responses for the intended target specific for the FluA and FluB assays. That is, the FluA assay detected influenza virus A but not influenza virus B, and the FluB assay detected influenza virus B but not influenza virus A. These results show that the FluA and FluB assays are specific for their intended influenza viral targets and do not cross-react with other human viral targets that are potentially found in respiratory samples.

EXAMPLE 3

Comparison of TMA-Based and PCR-Based Assays for Influenza Virus Detection

This example describes tests that compared the time for positive detection of influenza virus A and influenza virus B by using type-specific tests based on TMA and PCR amplification methods. The results show that TMA-based assays provided detection results sooner than obtained with assays based on real-time RT-PCR methods.

TMA-based FluA assays were performed substantially as described in Example 1, using primers of SEQ ID NO:9 (3 pmol/reaction) and SEQ ID NO:21 (15 pmol/reaction) to amplify target RNA transcripts of SEQ ID NO:1 (1 to 7 log copies per reaction), and detecting the amplicons by using a fluorophore-labeled probe of SEQ ID NO:29 (8 pmol/reaction). The primer of SEQ ID NO:21 was tested separately in two versions: one that was completely DNA, and one that was DNA except for LNA at residues 1 to 3. Six replicate assays were performed for each condition. The TMA-based FluB assay was performed substantially as described in Example 1, using primers of SEQ ID NO:39 (3 pmol/reaction) and SEQ ID NO:44 to amplify target RNA transcripts of SEQ ID NO:32 (1 to 7 log copies per reaction), and detecting the amplicons by using a fluorophore-labeled probe of SEQ ID NO:52 (8 pmol/reaction). Six replicate assays were performed for each condition.

Real-time RT-PCR assays for FluA were performed substantially as described above using primers of SEQ ID Nos. 68 and 69 to amplify the same RNA target used in the TMA-based FluA assay, and fluorophore-labeled probe of SEQ ID NO:70 to detect the PCR amplification products. Real-time RT-PCR assays for FluB were performed substantially as described above using primers of SEQ ID Nos. 71 and 72 to amplify the same RNA target used in the TMA-based FluB assay, and a fluorophore-labeled probe of SEQ ID NO:73 to detect the PCR amplification products. Each 50 µl reaction mixture contained include standard reagents (TAQMAN® One-Step RT-PCR Master Mix Reagents Kit, Applied Biosystems, Inc., Foster City, Calif.) and used conditions as suggested by the supplier, with the amplification and detection steps performed using a thermocycler and fluorometer device (OPTICON™ 2 system or CHROMO4™ Real-Time PCR Detector, Bio-Rad Laboratories, Inc., Hercules, Calif.).

The results of the comparative tests are shown in Table 5 for the FluA assays and Table 6 for the FluB assays. The results are shown as average (mean) emergence time for positive signals (± standard deviation, when calculated), determined from the initiation of the amplification reactions. The results show that, for both FluA and FluB targets, TMA-based assays provide a positive response before a positive response was seen for the PCR-based assays for the same number of targets. Results in Table 5 show that TMA-based FluA assays that used an LNA-containing primer had improved amplification kinetics compared to TMA-based assays that used a complete DNA primer, particularly for tests that contained fewer targets.

TABLE 5

Detection of Influenza Virus A

| Influenza virus A target (log copies) | Average Emergence Time ± SD (min) | | |
|---|---|---|---|
| | TMA (SEQ 21 DNA) | TMA (SEQ 21 LNA 1-3) | PCR |
| 1.00 | 32.5 ± 2.36 | 29.2 ± 1.91 | 55.0 ± 4.34 |
| 2.00 | 28.8 ± 2.09 | 25.3 ± 1.22 | 58.1 ± 0.45 |
| 3.00 | 28.8 ± 1.31 | 21.8 ± 0.20 | 55.0 ± 0.44 |
| 4.00 | 25.6 ± 0.38 | 19.8 ± 0.64 | 49.2 ± 0.37 |
| 5.00 | 23.2 ± 0.19 | 17.8 ± 0.18 | 44.6 ± 0.01 |
| 6.00 | 20.8 ± 0.10 | 15.7 ± 0.64 | 39.2 ± 0.41 |
| 7.00 | 18.7 ± 0.65 | 14.2 ± 0.29 | 33.8 ± 0.12 |

TABLE 6

Detection of Influenza Virus B

| Influenza virus B target | Average Emergence Time ± SD (min) | |
|---|---|---|
| (log copies) | TMA | PCR |
| 1.00 | 35.8 | 52.3 ± 0.14 |
| 2.00 | 36.0 ± 0.36 | 53.7 ± 0.52 |
| 3.00 | 32.7 ± 0.71 | 45.6 ± 0.14 |
| 4.00 | 29.8 ± 0.66 | 41.0 ± 0.07 |
| 5.00 | 25.7 ± 0.63 | 35.6 ± 0.06 |
| 6.00 | 22.4 ± 0.57 | 30.6 ± 0.13 |
| 7.00 | 19.2 ± 0.22 | 25.8 ± 0.07 |

In separate experiments, TMA-based FluB assays were performed similarly but using in separate reactions a promoter primer of SEQ ID NO:39 (3 pmol/reaction) combined with different synthetic versions of SEQ ID NO:44 primer (completely DNA, or DNA with LNA at positions 1 to 3, or DNA with LNA at positions 1 to 4, all used at 15 pmol/reaction). The reactions amplified FluB RNA transcript targets at 2.7 and 3.7 log copies per reaction and the amplicons were detected by using a fluorophore-labeled probe of SEQ ID NO:52. Results of these assays showed that the LNA-containing SEQ ID NO:44 primers improved amplification and assay kinetics compared to the completely DNA primer of SEQ ID NO:44.

EXAMPLE 4

Detection of Influenza Virus in Clinical Samples

This example shows that TMA-based FluA and FluB assays that detect the amplicons in real time provided positive results for samples that contain the target influenza virus sooner than for real-time RT-PCR-based assays performed on the same nineteen clinical samples. Assays were performed substantially as described in Example 3, but using an aliquot of prepared clinical sample nucleic acid in place of the target influenza virus RNA transcripts. Some of the TMA-based assays included an IC, substantially as described in Example 2. All assays included a negative control (no target) and positive controls (2 or 5 log copies of the intended target influenza virus RNA transcripts). All negative controls gave negative results.

The TMA-based FluA assays were performed substantially as described above but using an aliquot of prepared clinical sample nucleic acid in place of the FluA RNA transcripts as target. The assays used primers of SEQ ID Nos. 8 and 21, and a fluorophore-labeled probe of SEQ ID NO:29. The TMA-based assays performed with an IC included the IC target (200 copies of RNA transcript of SEQ ID NO:65), IC-specific primers of SEQ ID Nos. 61 and 62, and the IC-specific probe of SEQ ID NO:63. The RT-PCR FluA assays were performed substantially as described above but using an aliquot of prepared clinical sample nucleic acid in place of the FluA RNA transcripts as target. The RT-PCR FluA assays used primers of SEQ ID Nos. 68 and 69 and probe of SEQ ID NO:70 during 55 cycles of PCR amplification.

The TMA-based FluB assays were performed as described above but using an aliquot of prepared clinical sample nucleic acid in place of the FluB RNA transcripts as target. The assays used primers of SEQ ID Nos. 39 and 44, and a fluorophore-labeled probe of SEQ ID NO:48. The TMA-based assays performed with an IC included the IC target (200 copies of RNA transcript of SEQ ID NO:65), using IC-specific primers of SEQ ID Nos. 64 and 62, and the IC-specific probe of SEQ ID NO:63. The RT-PCR FluB assays were performed substantially as describe above but using an aliquot of prepared clinical sample nucleic acid in place of the FluB RNA transcripts as target. The RT-PCR FluB assays used primers of SEQ ID Nos. 71 and 72 and probe of SEQ ID NO:73 during 55 cycles of PCR amplification The FluA clinical samples were provided from a clinical testing laboratory (Warde Medical Center) and included an isolate of A/Beijing(H1N1) and other specimens or isolates obtained from patients during multiple influenza seasons. The FluB clinical samples represented six different isolates or specimens. Clinical samples were treated before amplification by purifying the nucleic acids in the samples using a non-specific method (QiAmp RNA extraction kits, using the supplier's recommended conditions). A 5 µl aliquot of the eluate containing nucleic acids isolated from the clinical samples was used per reaction.

The results of the FluA tests are shown in Table 7, and those of the FluB tests are shown in Table 8. The results in Table 7 show that the TMA-based and PCR-based assays provided consistent results for positive or negative specimens, and that the emergence times for the positive samples in the TMA-based assays were consistently earlier than for the same samples tested in the PCR-based assays, except for sample A1 tested using the TMA-based assay that included an IC. The negative specimen (A11) gave a positive result for the IC in the TMA-based assay, indicating that the result was a true negative for influenza virus A. The results in Table 8 similarly show that the TMA-based and PCR-based assays provided consistent positive results for the specimens but that the emergence times for the positive TMA-based assays were sooner than for the PCR-based assays. The total time required to perform the complete assay, i.e., not just emergence time of signal detected in the amplification reaction, was shorter for the TMA-based assays for both FluA and FluB (about 45 min) compared to PCR-based assays for the same targets (about 120 min).

TABLE 7

Detection of Influenza Virus A Amplified Nucleic Acid

| | Emergence Time (min) | | |
|---|---|---|---|
| Specimen | TMA without IC | TMA with IC | PCR without IC |
| A1 | 16.9 | 37.0 | 35.4 |
| A2 | 14.5 | 15.5 | 36.5 |
| A3 (A/Beijing (H1N1)) | 12.8 | 13.5 | 32.5 |
| A4 | 13.3 | 13.8 | 26.2 |
| A5 | 12.5 | 13.7 | 25.8 |
| A6 | 15.0 | 15.7 | 31.3 |
| A7 | 15.1 | 16.3 | 33.5 |
| A8 | 14.2 | 15.8 | 29.1 |
| A9 | 12.6 | 14.1 | 22.9 |
| A10 | 28.3 | 29.8 | 40.5 |
| A11 | negative | negative (IC positive) | negative |
| A12 | 14.0 | 14.8 | 30.1 |
| A13 | 14.9 | 15.7 | 27.6 |
| A14 | 11.1 | 11.6 | 24.5 |
| A15 | 12.1 | 12.7 | 28.4 |
| A16 | 11.6 | 12.8 | 29.3 |
| A17 | 13.6 | 15.0 | 27.6 |
| A18 | 11.1 | 12.1 | 30.0 |
| 19 | 13.0 | 14.2 | 33.5 |
| Positive control ($10^2$ copies) | 20.9 | 35.7 | 37.7 |
| Positive control ($10^5$ copies) | 15.3 | 16.5 | 32.4 |

TABLE 8

Detection of Influenza Virus B Amplified Nucleic Acid

| | Emergence Time (min) | | |
|---|---|---|---|
| Specimen | TMA without IC | TMA with IC | PCR without IC |
| B1 | 13.8 | 14.4 | 27.8 |
| B2 | 13.8 | 16.3 | 26.3 |
| B3 | 16.2 | 20.3 | 30.8 |
| B4 | 17.8 | 23.3 | 30.9 |
| B5 | 21.1 | 29.4 | 33.6 |
| B6 | 13.6 | 16.2 | 27.6 |
| Positive control ($10^2$ copies) | 24.5 | 24.6 | 50.4 |
| Positive control ($10^5$ copies) | 16.5 | 16.8 | Not tested |

EXAMPLE 5

Detection of Amplified Sequences of Influenza Viruses by Using Chemiluminescent Probes This example demonstrates assays that involved transcription associated amplification of influenza virus A or influenza virus B nucleic acids followed by detection of the amplification products by using AE-labeled probes specific for the influenza virus A or influenza virus B amplified sequences. The probes hybridized to the amplicons emit chemiluminescent signals that are detected in a homogeneous assay format.

For TMA-based FluA assays, standard TMA reactions were performed to amplify sequences in 500,000 copies of the FluA target RNA (transcript of SEQ ID NO:1) by using different combinations of two primers (SEQ ID No. 7, 9, or 11 combined with SEQ ID No. 21, 22, or 24). Following amplification, hybridization to a probe of SEQ ID NO:26 labeled with AE between residues 7 and 8 was used to detect amplicons produced in the TMA reaction. Negative controls were assays performed identically but in reaction mixtures that contained no FluA target RNA. Following amplification, the amplicons were hybridized to the AE-labeled probe in hybridization reagent at 60° C. for 30 min and then cooled to room temperature for 5 min. Then, AE labels in unbound probes were selectively hydrolyzed by using selection reagent and incubation at 60° C. for 10 min, followed by room temperature for 15 min. Chemiluminescent signals were elicited by using detect reagent 1, followed by neutralization with detect reagent 11, and chemiluminescence was detected on a luminometer (LEADER® HC, Gen-Probe Incorporated) as relative light units (RLU)) substantially as described previously (U.S. Pat. Nos. 5,283,174 and 5,656,744, Arnold et al., and U.S. Pat. No. 5,658,737, Nelson et al., at column 25, lines 27-46; Nelson et al., 1996, Biochem. 35:8429-8438 at 8432). The results of the assays are shown in Table 9. The results show that a homogeneous chemiluminescent detection system also detects influenza virus A nucleic acid following transcription associated amplification by using different combinations of FluA-specific amplification oligomers.

TABLE 9

Detection of Influenza Virus A Amplified Nucleic Acid

| Primers (SEQ ID NOs) | RLU for FluA Positive Sample | RLU for Negative Control |
|---|---|---|
| 7 and 21 | $4.92 \times 10^6$ | $2.76 \times 10^3$ |
| 9 and 21 | $4.83 \times 10^6$ | $2.74 \times 10^3$ |
| 11 and 21 | $4.00 \times 10^6$ | $2.80 \times 10^3$ |
| 7 and 22 | $4.84 \times 10^6$ | $2.95 \times 10^3$ |
| 9 and 22 | $3.56 \times 10^6$ | $2.65 \times 10^3$ |
| 11 and 22 | $4.25 \times 10^6$ | $2.74 \times 10^3$ |
| 7 and 24 | $3.82 \times 10^6$ | $2.69 \times 10^3$ |
| 9 and 24 | $2.35 \times 10^6$ | $2.74 \times 10^3$ |
| 11 and 24 | $1.48 \times 10^6$ | $2.56 \times 10^3$ |

Probes specific for FluB target sequences were similarly shown to specifically detect influenza virus B sequences. In these assays, a synthetic RNA target (SEQ ID NO:33, at 2 pmol/reaction) was mixed with AE-labeled probes of SEQ ID NO:48 (labeled between residues 8 and 9), SEQ ID NO:49 (labeled between residues 9 and 10), and SEQ ID NO:50 (labeled between residues 7 and 8) in a mixture that mimics a TMA reaction mixture, and then the detection step was performed substantially as described above. That is, detection of the FluB target sequences was performed directly without amplication from an initial RNA target. The average results of these assays (n=5 for each condition) are shown in Table 10. These results show that influenza virus B target sequences are detected by using AE-labeled probes in conditions similar to those that result from amplification in a TMA-based assay.

TABLE 10

Detection of Influenza Virus B Amplified Nucleic Acid

| FluB AE-labeled Probe | RLU for FluB Positive Samples | RLU for Negative Controls |
|---|---|---|
| SEQ ID NO: 49 | $6.91 \times 10^5$ | $1.53 \times 10^3$ |
| SEQ ID NO: 50 | $2.18 \times 10^5$ | $1.16 \times 10^3$ |
| SEQ ID NO: 48 | $2.10 \times 10^6$ | $8.91 \times 10^2$ |

EXAMPLE 6

TMA-Based Assays for Influenza Virus Detection

This example shows that TMA-based FluA and FluB assays give comparable results for influenza virus detection when performed manually or by using an automated device. For both FluA and FluB assays, the method steps were performed using identical conditions but each assay contained the target-specific oligomers for the respective target of the assay, influenza virus A or influenza virus B.

Samples were prepared containing synthetic targets for the respective assays (RNA transcripts of SEQ ID NO:1 for FluA assays, or RNA transcripts of SEQ ID NO:32 for FluB assays, at 0, 250, 500, 1000 or 5000 copies/ml) and mixed with target capture reagent (TCR) in a final volume of 0.5 ml containing a target capture probe (200 pmol/ml) specific for the respective influenza virus target (SEQ ID NO:6 for FluA assays, and SEQ ID NO:35 for FluB assays). Target capture was performed by incubating the mixture containing the target RNA, capture probe and TCR at 62° C. for 30, and then at room temperature for 30 min. Magnetic particles with captured influenza virus nucleic acids were separated to an inner portion of the container by using a magnetic field, and the sample liquid was removed. Captured target nucleic acids on the particles were washed with 1 ml/reaction of Wash Solution, particles were separated magnetically, and the Wash Solution was removed. Washed particles with captured influenza viral target nucleic acids were suspended in 75 µl of a nucleic acid amplification reagent for TMA containing the appropriate amplification oligomers (SEQ ID NO:10 at 300 pmol/ml, and SEQ ID NO:21 with LNA at residues 1 to 3 at 500 pmol/ml for FluA assays; SEQ ID NO:39 at 300 pmol/ml, and SEQ ID NO:44 with LNA at residues 1 to 3 at 500 pmol/ml for FluB assays). TMA reactions were incubated at 62° C. for 10 min, then at 42° C. for 5 min, and TMA enzymes were added, mixed, and incubation continued at 42° C. for 60 min. Detection was performed substantially as described in Example 5 using AE-labeled probes specific for the intended target of the assay (SEQ ID NO:26 at $5\times10^7$ RLU/ml for FluA assays, and SEQ ID NO:48 at $5\times10^7$ RLU/ml for FluB assays), and chemiluminescent signals produced in the homogeneous assay format were detected and measured.

Figure 2:
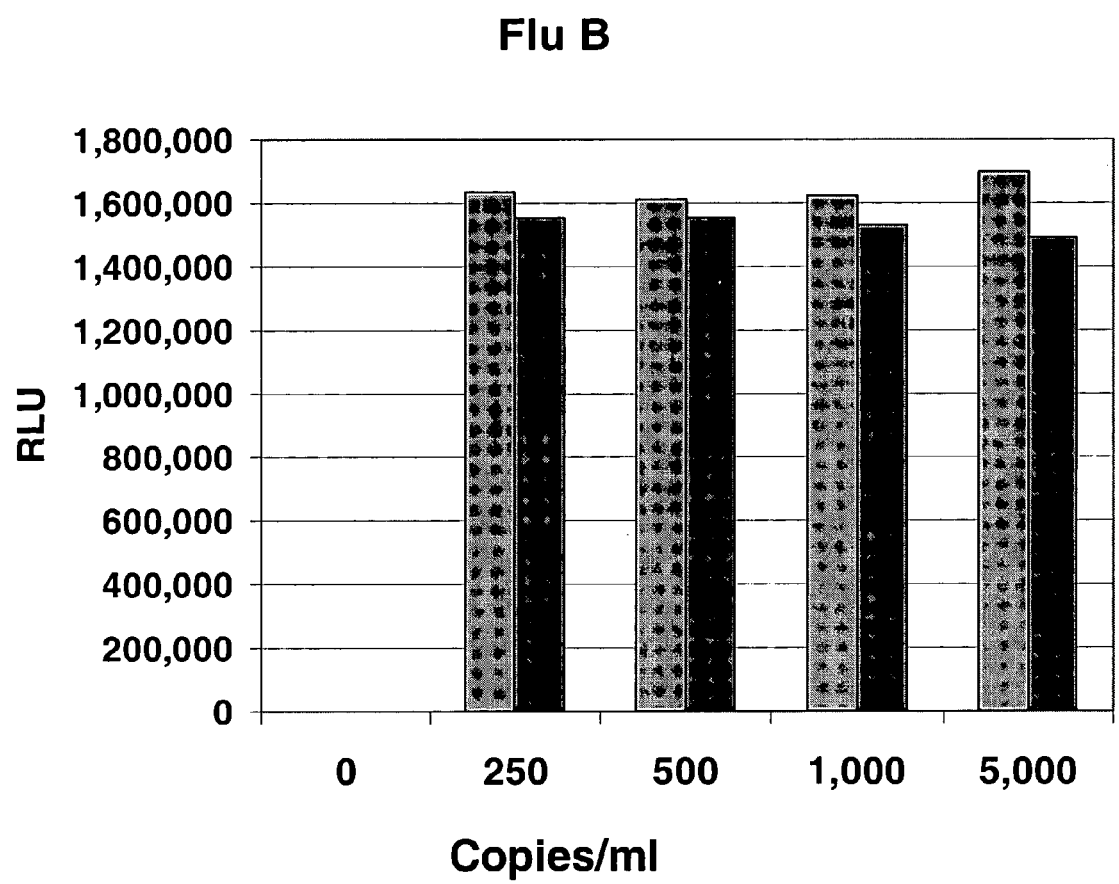
FIG. 2 is a bar graph showing signal detected (relative light units, RLU) for different amounts of influenza virus B target (250 to 5000 copies per ml) in TMA-based assays performed manually (light bars) or by using an automated system (dark bars).

The FluA and FluB assays were performed separately using 10 replicates for each assay condition. The assay steps were performed manually or by using an automated system (for details see U.S. Pat. Nos. 6,605,213 and 6,846,456). The results of these assays are shown in FIG. 1 for FluA assays and FIG. 2 for FluB assays. FIG. 1 graphs the signals (average RLU) detected in the TMA-based FluA assays for each tested amount of influenza virus A target (250 to 5000 copies/ml) in assays performed manually (light bars) or by using an automated system (dark bars). FIG. 2 graphs the signals (average RLU) detected in TMA-based FluB assays for each tested amount of influenza virus B target (250 to 5000 copies/ml) in assays performed manually (light bars) or by using an automated system (dark bars). The results shown in FIGS. 1 and 2 illustrate that both TMA-based assays detected 250 copies/ml or greater of the respective intended target influenza virus nucleic acids, whether the steps were performed manually or in an automated system.

We claim:

1. A composition comprising at least two isolated nucleic acid oligomers specific for influenza virus B consisting of SEQ ID NO:39 and SEQ ID NO:44, or completely complementary sequences to SEQ ID NO:39 and SEQ ID NO:44.

2. The composition of claim 1, wherein the two nucleic acid oligomers include an oligomer consisting of SEQ ID NO:44.

3. The composition of claim 1, that further includes at least one oligomer consisting of SEQ ID NO:48.

4. The composition of claim 1, wherein the at least two nucleic acid oligomers specific for influenza virus B are in the form of a kit.

5. A method of detecting nucleic acid of influenza virus B in a sample, comprising the steps of:
   providing a sample containing influenza virus B nucleic acid;
   amplifying a target sequence in the influenza virus B nucleic acid contained in the sample by using a nucleic acid polymerase and at least two isolated nucleic acid oligomers consisting of the sequences of SEQ ID Nos. 39 and 44, or the complete complements of the sequences consisting of SEQ ID Nos. 39 and 44 in vitro to produce an amplified product under substantially isothermal conditions, and
   detecting the amplified product, thereby detecting the presence of influenza virus B in the sample.

6. The method of claim 5, wherein amplifying the target sequence in the influenza virus B nucleic acid uses at least one oligomer consisting of the sequence of SEQ ID NO:39 and one oligomer consisting of the sequence of SEQ ID NO:44.

7. The method of claim 5, wherein the detecting step uses at least one probe consisting of SEQ ID NO:48 that includes at least one 2'-methoxy RNA group to detect the amplified product of the target sequence of influenza virus B.

8. The method of claim 5, further including the steps of providing an internal control oligomer, amplifying a target sequence contained in the internal control oligomer, and detecting the amplified product made from the internal control oligomer, thereby indicating that the amplifying and detecting steps of the method were properly performed.

9. The method of claim 5, further including a step of isolating the influenza virus B nucleic acid from the sample before the amplifying step.

10. The method of claim 5, wherein the target sequence is contained in the sequence consisting of SEQ ID NO:32, the complete complement of the sequence consisting of SEQ ID NO:32, the RNA equivalent of the sequence consisting of SEQ ID NO:32, or the RNA equivalent of the complete complement of the sequence consisting of SEQ ID NO:32.

11. The method of claim 5, wherein the detecting step uses a probe that detects the amplified product in a homogeneous assay system.

12. A composition comprising at least two isolated nucleic acid oligomers specific for influenza virus B wherein one oligomer has a target hybridizing sequence that is from 19 to 21 nucleotides in length and contains a sequences consisting essentially of SEQ ID NO:42, the complement and/or RNA equivalent thereof and, optionally, contains at least one 2' methoxy RNA group or at least one LNA; and wherein a second oligomer has a sequence that is from 19 to 22 nucleotides in length and contains a sequence consisting essentially of SEQ ID NO:44, the complement and/or RNA equivalent thereof and, optionally, contains at least one 2' methoxy RNA group or at least one LNA.

13. The composition of claim 12, wherein a third oligomer has a sequence consisting of SEQ ID NO:48, the completely complementary sequence of SEQ ID NO:48 and, optionally, at least one detectable label joined directly or indirectly to the oligomer sequence.

14. The composition of claim 13, wherein the label is detectable in a homogenous assay system.

15. The composition of claim 13, wherein the label is an acridinium ester compound.

16. The composition of claim 12, wherein 5' positions 1 to 3 of the SEQ ID NO:44 sequence are in an LNA conformation.

17. The composition of claim 12, wherein 5' positions 1 to 4 of the SEQ ID NO:44 sequence are in an LNA conformation.

18. The composition of claim 12, wherein the at least two nucleic acid oligomers specific for influenza virus B are in the form of a kit.

19. A method of detecting nucleic acid of influenza virus B in a sample, comprising the steps of:
   providing a sample containing influenza virus B nucleic acid;
   amplifying a target sequence in the influenza virus B nucleic acid contained in the sample by using a nucleic acid polymerase and at least two isolated nucleic acid amplification oligomers, wherein the at least two nucleic acid amplification oligomers includes an amplification oligomer 19 to 21 nucleotides in length consisting essentially of the nucleotide target hybridizing sequences of SEQ ID NO:42, the complement and/or RNA equivalent thereof and, optionally, contains at least one 2' methoxy RNA group or at least one LNA, and wherein the at least two nucleic acid amplification oligomers includes an amplification oligomer 19 to 22 nucleotides in length consisting essentially of the nucleotide sequences of SEQ ID NO:44, the complement and/or RNA equivalent thereof and, optionally, contains at least one 2' methoxy RNA group or at least one LNA, in vitro to produce an amplified product under substantially isothermal conditions, and
   detecting the amplified product, thereby detecting the presence of influenza virus B in the sample.

20. The method of claim 19, wherein the detecting step uses at least one probe consisting of SEQ ID NO:48 that includes at least one 2'-methoxy RNA group to detect the amplified product of the target sequence of influenza virus B.

21. The method of claim 19, further including the steps of providing an internal control oligomer, amplifying a target sequence contained in the internal control oligomer, and detecting the amplified product made from the internal control oligomer, thereby indicating that the amplifying and detecting steps of the method were properly performed.

22. The method of claim 19, further including a step of isolating the influenza virus B nucleic acid from the sample before the amplifying step.

23. The method of claim 19, wherein the target sequence is contained in the sequence consisting of SEQ ID NO:32, the complete complement of the sequence consisting of SEQ ID NO:32, the RNA equivalent of the sequence consisting of SEQ ID NO:32, or the RNA equivalent of the complete complement of the sequence consisting of SEQ ID NO:32.

24. The method of claim 19, wherein 5' positions 1 to 3 of the oligomer consisting of SEQ ID NO:44 are in a locked nucleic acid (LNA) conformation.

25. The method of claim 19, wherein 5' positions 1 to 4 of the oligomer consisting of SEQ ID NO:44 are in a locked nucleic acid (LNA) conformation.

26. The method of claim 19, wherein the detecting step uses a probe that detects the amplified product in a homogeneous assay system.

27. The method of claim 19, wherein the detecting step uses at least one probe consisting of SEQ ID NO:48 that includes at least one 2'-methoxy RNA group, at least one detectable label or both, to detect the amplified product of the target sequence of influenza virus B.

28. The method of claim 27 wherein the detectable label is an acridinium ester compound.

29. : The method of claim 19, wherein the amplification oligomer 19 to 21 nucleotides in length consisting essentially of the nucleotide target hybridizing sequences of SEQ ID NO:42, the complement and/or RNA equivalent thereof and, optionally, contains at least one 2' methoxy RNA group or at least one LNA, further includes a 5' promoter sequence that is SEQ ID NO19 or SEQ ID NO:20.

30. The composition of claim 12, wherein the oligomer that has a target hybridizing sequence that is from 19 to 21 nucleotides in length and contains a sequences consisting essentially of SEQ ID NO:42 , the complement and/or RNA equivalent thereof and, optionally, contains at least one 2' methoxy RNA group or at least one LNA, further includes a 5' promoter sequence that is SEQ ID NO19 or SEQ ID NO:20.

* * * * *